（12) United States Patent
Bailly et al.

(10) Patent No.: US 9,622,843 B2
(45) Date of Patent: Apr. 18, 2017

(54) UMBILICAL HERNIA PROSTHESIS

(75) Inventors: Pierre Bailly, Caluire-et-Cuire (FR); Gaëtan Romuald, Bron (FR)

(73) Assignee: SOFRADIM PRODUCTION, Trevoux (FR)

(*) Notice: Subject to any disclaimer, the term of this patent is extended or adjusted under 35 U.S.C. 154(b) by 406 days.

(21) Appl. No.: 14/232,390

(22) PCT Filed: Jun. 29, 2012

(86) PCT No.: PCT/EP2012/062671
§ 371 (c)(1),
(2), (4) Date: Mar. 24, 2014

(87) PCT Pub. No.: WO2013/007534
PCT Pub. Date: Jan. 17, 2013

(65) Prior Publication Data
US 2014/0194926 A1    Jul. 10, 2014

(30) Foreign Application Priority Data

Jul. 13, 2011 (FR) .................................... 11 56426

(51) Int. Cl.
*A61F 2/00*    (2006.01)
*A61B 17/00*    (2006.01)
(Continued)

(52) U.S. Cl.
CPC ........ *A61F 2/0063* (2013.01); *A61B 17/0057* (2013.01); *A61B 17/04* (2013.01);
(Continued)

(58) Field of Classification Search
CPC ...... A61B 17/0057; A61B 2017/00597; A61B 2017/00637; A61B 2017/00641;
(Continued)

(56) References Cited

U.S. PATENT DOCUMENTS 1,187,158 A    6/1916 Mcginley
3,054,406 A    9/1962 Usher
(Continued)

FOREIGN PATENT DOCUMENTS

CA    1317836 C    5/1993
CN    101489502 A    7/2009
(Continued)

OTHER PUBLICATIONS

Chinese Office Action, Application No. 2012800347410 dated Mar. 30, 2015.
(Continued)

*Primary Examiner* — Ryan J Severson

(57) ABSTRACT

The present disclosure relates to a prosthesis comprising: —at least one flexible mesh delimited by a peripheral exterior edge, —at least two tongues extending from one face of the mesh, and —at least one member for reinforcing said mesh, characterized in that said reinforcing member takes the form of a frame fastened to said mesh and substantially adopting the shape of said peripheral exterior edge of the mesh, said frame being set back from said peripheral exterior edge and being provided with two hinge points, the line passing through said two hinge points also passing through the center of the mesh and thus forming a line for folding the mesh in two.

20 Claims, 11 Drawing Sheets

Figure 1:
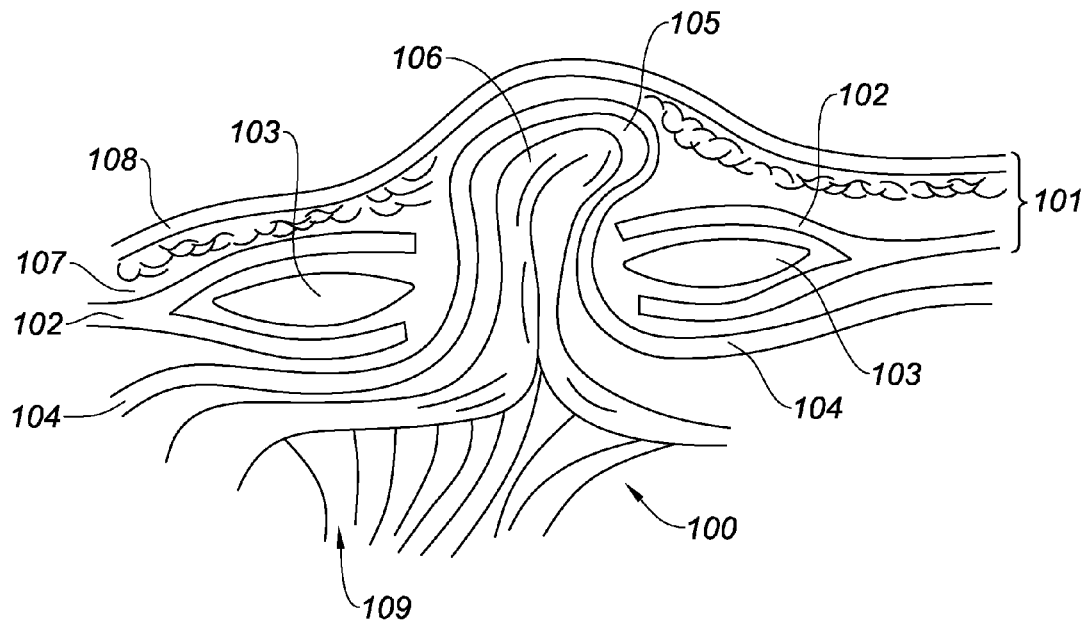

(51) Int. Cl.
  *A61B 17/04* (2006.01)
  *A61B 17/06* (2006.01)
(52) U.S. Cl.
  CPC ..... *A61B 17/06* (2013.01); *A61B 2017/00597* (2013.01); *A61B 2017/00623* (2013.01); *A61B 2017/0496* (2013.01); *A61F 2210/0014* (2013.01); *A61F 2250/0031* (2013.01); *A61F 2250/0097* (2013.01)
(58) Field of Classification Search
  CPC ................. A61F 2/0063; A61F 2/0077; A61F 2002/0068; A61F 2002/009; A61F 2002/0091; A61F 2250/0097
  See application file for complete search history.

(56) References Cited

U.S. PATENT DOCUMENTS

| | | |
|---|---|---|
| 3,118,294 A | 1/1964 | Van Laethem |
| 3,124,136 A | 3/1964 | Usher |
| 3,272,204 A | 9/1966 | Charles et al. |
| 3,276,448 A | 10/1966 | Usher |
| 3,320,649 A | 5/1967 | Naimer |
| 3,364,200 A | 1/1968 | Ashton et al. |
| 3,570,482 A | 3/1971 | Emoto et al. |
| 3,718,725 A | 2/1973 | Hamano |
| 3,887,699 A | 6/1975 | Yolles |
| 4,006,747 A | 2/1977 | Kronenthal et al. |
| 4,060,081 A | 11/1977 | Yannas et al. |
| 4,173,131 A | 11/1979 | Pendergrass et al. |
| 4,193,137 A | 3/1980 | Heck |
| 4,248,064 A | 2/1981 | Odham |
| 4,294,241 A | 10/1981 | Miyata |
| 4,307,717 A | 12/1981 | Hymes et al. |
| 4,338,800 A | 7/1982 | Matsuda |
| 4,476,697 A | 10/1984 | Schafer et al. |
| 4,487,865 A | 12/1984 | Balazs et al. |
| 4,500,676 A | 2/1985 | Balazs et al. |
| 4,511,653 A | 4/1985 | Play et al. |
| 4,527,404 A | 7/1985 | Nakagaki et al. |
| 4,591,501 A | 5/1986 | Cioca |
| 4,597,762 A | 7/1986 | Walter et al. |
| 4,603,695 A | 8/1986 | Ikada et al. |
| 4,631,932 A | 12/1986 | Sommers |
| 4,670,014 A | 6/1987 | Huc et al. |
| 4,709,562 A | 12/1987 | Matsuda |
| 4,748,078 A | 5/1988 | Doi et al. |
| 4,759,354 A | 7/1988 | Quarfoot |
| 4,767,628 A | 8/1988 | Hutchinson |
| 4,769,038 A | 9/1988 | Bendavid et al. |
| 4,796,603 A | 1/1989 | Dahlke et al. |
| 4,813,942 A | 3/1989 | Alvarez |
| 4,841,962 A | 6/1989 | Berg et al. |
| 4,854,316 A | 8/1989 | Davis |
| 4,925,294 A | 5/1990 | Geshwind et al. |
| 4,931,546 A | 6/1990 | Tardy et al. |
| 4,942,875 A | 7/1990 | Hlavacek et al. |
| 4,948,540 A | 8/1990 | Nigam |
| 4,950,483 A | 8/1990 | Ksander et al. |
| 4,970,298 A | 11/1990 | Silver et al. |
| 4,976,737 A | 12/1990 | Leake |
| 5,002,551 A | 3/1991 | Linsky et al. |
| 5,015,584 A | 5/1991 | Brysk |
| 5,106,629 A | 4/1992 | Cartmell et al. |
| 5,116,357 A | 5/1992 | Eberbach |
| 5,147,374 A | 9/1992 | Fernandez |
| 5,162,430 A | 11/1992 | Rhee et al. |
| 5,171,273 A | 12/1992 | Silver et al. |
| 5,176,692 A | 1/1993 | Wilk et al. |
| 5,192,301 A | 3/1993 | Kamiya et al. |
| 5,195,542 A | 3/1993 | Gazielly et al. |
| 5,196,185 A | 3/1993 | Silver et al. |
| 5,201,745 A | 4/1993 | Tayot et al. |
| 5,201,764 A | 4/1993 | Kelman et al. |
| 5,206,028 A | 4/1993 | Li |
| 5,217,493 A | 6/1993 | Raad et al. |
| 5,254,133 A | 10/1993 | Seid |
| 5,256,418 A | 10/1993 | Kemp et al. |
| 5,258,000 A | 11/1993 | Gianturco |
| 5,263,983 A | 11/1993 | Yoshizato et al. |
| 5,304,595 A | 4/1994 | Rhee et al. |
| 5,306,500 A | 4/1994 | Rhee et al. |
| 5,324,775 A | 6/1994 | Rhee et al. |
| 5,328,955 A | 7/1994 | Rhee et al. |
| 5,334,527 A | 8/1994 | Brysk |
| 5,339,657 A | 8/1994 | McMurray |
| 5,350,583 A | 9/1994 | Yoshizato et al. |
| 5,356,432 A | 10/1994 | Rutkow et al. |
| 5,368,549 A | 11/1994 | McVicker |
| 5,368,602 A | 11/1994 | de la Torre |
| 5,370,650 A | 12/1994 | Tovey et al. |
| 5,376,375 A | 12/1994 | Rhee et al. |
| 5,376,376 A | 12/1994 | Li |
| 5,397,331 A | 3/1995 | Himpens et al. |
| 5,399,361 A | 3/1995 | Song et al. |
| 5,413,791 A | 5/1995 | Rhee et al. |
| 5,425,740 A | 6/1995 | Hutchinson, Jr. |
| 5,428,022 A | 6/1995 | Palefsky et al. |
| 5,433,996 A | 7/1995 | Kranzler et al. |
| 5,441,491 A | 8/1995 | Verschoor et al. |
| 5,441,508 A | 8/1995 | Gazielly et al. |
| 5,456,693 A | 10/1995 | Conston et al. |
| 5,456,711 A | 10/1995 | Hudson |
| 5,466,462 A | 11/1995 | Rosenthal et al. |
| 5,480,644 A | 1/1996 | Freed |
| 5,487,895 A | 1/1996 | Dapper et al. |
| 5,490,984 A | 2/1996 | Freed |
| 5,512,291 A | 4/1996 | Li |
| 5,512,301 A | 4/1996 | Song et al. |
| 5,514,181 A | 5/1996 | Light et al. |
| 5,522,840 A | 6/1996 | Krajicek |
| 5,523,348 A | 6/1996 | Rhee et al. |
| 5,536,656 A | 7/1996 | Kemp et al. |
| 5,543,441 A | 8/1996 | Rhee et al. |
| 5,565,210 A | 10/1996 | Rosenthal et al. |
| 5,567,806 A | 10/1996 | Abdul-Malak et al. |
| 5,569,273 A | 10/1996 | Titone et al. |
| RE35,399 E | 12/1996 | Eisenberg |
| 5,593,441 A | 1/1997 | Lichtenstein et al. |
| 5,595,621 A | 1/1997 | Light et al. |
| 5,601,571 A | 2/1997 | Moss |
| 5,607,474 A | 3/1997 | Athanasiou et al. |
| 5,607,590 A | 3/1997 | Shimizu |
| 5,614,587 A | 3/1997 | Rhee et al. |
| 5,618,551 A | 4/1997 | Tardy et al. |
| 5,634,931 A | 6/1997 | Kugel |
| 5,639,796 A | 6/1997 | Lee |
| 5,665,391 A | 9/1997 | Lea |
| 5,667,839 A | 9/1997 | Berg |
| 5,676,967 A | 10/1997 | Williams et al. |
| 5,681,568 A | 10/1997 | Goldin et al. |
| 5,686,115 A | 11/1997 | Vournakis et al. |
| 5,690,675 A | 11/1997 | Sawyer et al. |
| 5,695,525 A | 12/1997 | Mulhauser et al. |
| 5,697,978 A | 12/1997 | Sgro |
| 5,700,476 A | 12/1997 | Rosenthal et al. |
| 5,700,477 A | 12/1997 | Rosenthal et al. |
| 5,702,416 A | 12/1997 | Kieturakis et al. |
| 5,709,934 A | 1/1998 | Bell et al. |
| 5,711,960 A | 1/1998 | Shikinami |
| 5,716,409 A | 2/1998 | Debbas |
| 5,720,981 A | 2/1998 | Eisinger |
| 5,732,572 A | 3/1998 | Litton |
| 5,743,917 A | 4/1998 | Saxon |
| 5,749,895 A | 5/1998 | Sawyer et al. |
| 5,752,974 A | 5/1998 | Rhee et al. |
| 5,766,246 A | 6/1998 | Mulhauser et al. |
| 5,766,631 A | 6/1998 | Arnold |
| 5,769,864 A | 6/1998 | Kugel |
| 5,771,716 A | 6/1998 | Schlussel |
| 5,785,983 A | 7/1998 | Furlan et al. |
| 5,800,541 A | 9/1998 | Rhee et al. |
| 5,814,328 A | 9/1998 | Gunasekaran |
| 5,833,705 A | 11/1998 | Ken et al. |

(56) References Cited

U.S. PATENT DOCUMENTS

| | | |
|---|---|---|
| 5,840,011 A | 11/1998 | Landgrebe et al. |
| 5,861,034 A | 1/1999 | Taira et al. |
| 5,863,984 A | 1/1999 | Doillon et al. |
| 5,869,080 A | 2/1999 | McGregor et al. |
| 5,871,767 A | 2/1999 | Dionne et al. |
| 5,876,444 A | 3/1999 | Lai |
| 5,891,558 A | 4/1999 | Bell et al. |
| 5,899,909 A | 5/1999 | Claren et al. |
| 5,906,937 A | 5/1999 | Sugiyama et al. |
| 5,910,149 A | 6/1999 | Kuzmak |
| 5,911,731 A | 6/1999 | Pham et al. |
| 5,916,225 A | 6/1999 | Kugel |
| 5,919,232 A | 7/1999 | Chaffringeon et al. |
| 5,919,233 A | 7/1999 | Knopf et al. |
| 5,922,026 A | 7/1999 | Chin |
| 5,931,165 A | 8/1999 | Reich et al. |
| 5,942,278 A | 8/1999 | Hagedorn et al. |
| 5,962,136 A | 10/1999 | Dewez et al. |
| 5,972,022 A | 10/1999 | Huxel |
| RE36,370 E | 11/1999 | Li |
| 5,993,844 A | 11/1999 | Abraham et al. |
| 5,994,325 A | 11/1999 | Roufa et al. |
| 5,997,895 A | 12/1999 | Narotam et al. |
| 6,001,895 A | 12/1999 | Harvey et al. |
| 6,008,292 A | 12/1999 | Lee et al. |
| 6,015,844 A | 1/2000 | Harvey et al. |
| 6,039,686 A | 3/2000 | Kovac |
| 6,042,534 A | 3/2000 | Gellman et al. |
| 6,042,592 A | 3/2000 | Schmitt |
| 6,043,089 A | 3/2000 | Sugiyama et al. |
| 6,051,425 A | 4/2000 | Morota et al. |
| 6,056,688 A | 5/2000 | Benderev et al. |
| 6,056,970 A | 5/2000 | Greenawalt et al. |
| 6,057,148 A | 5/2000 | Sugiyama et al. |
| 6,063,396 A | 5/2000 | Kelleher |
| 6,066,776 A | 5/2000 | Goodwin et al. |
| 6,066,777 A | 5/2000 | Benchetrit |
| 6,071,292 A | 6/2000 | Makower et al. |
| 6,077,281 A | 6/2000 | Das |
| 6,080,194 A | 6/2000 | Pachence et al. |
| 6,083,522 A | 7/2000 | Chu et al. |
| 6,090,116 A | 7/2000 | D'Aversa et al. |
| 6,113,623 A | 9/2000 | Sgro |
| 6,120,539 A | 9/2000 | Eldridge et al. |
| 6,132,765 A | 10/2000 | DiCosmo et al. |
| 6,143,037 A | 11/2000 | Goldstein et al. |
| 6,153,292 A | 11/2000 | Bell et al. |
| 6,162,962 A | 12/2000 | Hinsch et al. |
| 6,165,488 A | 12/2000 | Tardy et al. |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,179,872 B1 | 1/2001 | Bell et al. |
| 6,180,848 B1 | 1/2001 | Flament et al. |
| 6,197,325 B1 | 3/2001 | MacPhee et al. |
| 6,197,934 B1 | 3/2001 | DeVore et al. |
| 6,197,935 B1 | 3/2001 | Doillon et al. |
| 6,201,439 B1 | 3/2001 | Ishida et al. |
| 6,210,439 B1 | 4/2001 | Firmin et al. |
| 6,214,020 B1 | 4/2001 | Mulhauser et al. |
| 6,221,109 B1 | 4/2001 | Geistlich et al. |
| 6,224,616 B1 | 5/2001 | Kugel |
| 6,241,768 B1 | 6/2001 | Agarwal et al. |
| 6,258,124 B1 | 7/2001 | Darois et al. |
| 6,262,332 B1 | 7/2001 | Ketharanathan |
| 6,264,702 B1 | 7/2001 | Ory et al. |
| 6,267,772 B1 | 7/2001 | Mulhauser et al. |
| 6,270,530 B1 | 8/2001 | Eldridge et al. |
| 6,270,792 B1 | 8/2001 | Guillemet et al. |
| 6,277,397 B1 | 8/2001 | Shimizu |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,306,079 B1 | 10/2001 | Trabucco |
| 6,306,424 B1 | 10/2001 | Vyakarnam et al. |
| 6,312,474 B1 | 11/2001 | Francis et al. |
| 6,319,264 B1 | 11/2001 | Tormala et al. |
| 6,328,686 B1 | 12/2001 | Kovac |
| 6,334,872 B1 | 1/2002 | Termin et al. |
| 6,371,975 B2 | 4/2002 | Cruise et al. |
| 6,383,201 B1 | 5/2002 | Dong |
| 6,391,060 B1 | 5/2002 | Ory et al. |
| 6,391,333 B1 | 5/2002 | Li et al. |
| 6,391,939 B2 | 5/2002 | Tayot et al. |
| 6,408,656 B1 | 6/2002 | Ory et al. |
| 6,410,044 B1 | 6/2002 | Chudzik et al. |
| 6,413,742 B1 | 7/2002 | Olsen et al. |
| 6,425,924 B1 | 7/2002 | Rousseau |
| 6,428,978 B1 | 8/2002 | Olsen et al. |
| 6,436,030 B2 | 8/2002 | Rehil |
| 6,440,167 B2 | 8/2002 | Shimizu |
| 6,443,964 B1 | 9/2002 | Ory et al. |
| 6,447,551 B1 | 9/2002 | Goldmann |
| 6,447,802 B2 | 9/2002 | Sessions et al. |
| 6,448,378 B2 | 9/2002 | DeVore et al. |
| 6,451,032 B1 | 9/2002 | Ory et al. |
| 6,451,301 B1 | 9/2002 | Sessions et al. |
| 6,454,787 B1 | 9/2002 | Maddalo et al. |
| 6,458,889 B1 | 10/2002 | Trollsas et al. |
| 6,477,865 B1 | 11/2002 | Matsumoto |
| 6,479,072 B1 | 11/2002 | Morgan et al. |
| 6,485,503 B2 | 11/2002 | Jacobs et al. |
| 6,500,464 B2 | 12/2002 | Ceres et al. |
| 6,500,777 B1 | 12/2002 | Wiseman et al. |
| 6,509,031 B1 | 1/2003 | Miller et al. |
| 6,511,958 B1 | 1/2003 | Atkinson et al. |
| 6,514,286 B1 | 2/2003 | Leatherbury et al. |
| 6,514,514 B1 | 2/2003 | Atkinson et al. |
| 6,540,773 B2 | 4/2003 | Dong |
| 6,541,023 B1 | 4/2003 | Andre et al. |
| 6,548,077 B1 | 4/2003 | Gunasekaran |
| 6,554,855 B1 | 4/2003 | Dong |
| 6,559,119 B1 | 5/2003 | Burgess et al. |
| 6,566,345 B2 | 5/2003 | Miller et al. |
| 6,575,988 B2 | 6/2003 | Rousseau |
| 6,576,019 B1 | 6/2003 | Atala |
| 6,596,002 B2 | 7/2003 | Therin et al. |
| 6,596,304 B1 | 7/2003 | Bayon et al. |
| 6,599,323 B2 | 7/2003 | Melican et al. |
| 6,599,524 B2 | 7/2003 | Li et al. |
| 6,599,690 B1 | 7/2003 | Abraham et al. |
| 6,610,006 B1 | 8/2003 | Amid et al. |
| 6,613,348 B1 | 9/2003 | Jain |
| 6,616,685 B2 | 9/2003 | Rousseau |
| 6,623,963 B1 | 9/2003 | Muller et al. |
| 6,630,414 B1 | 10/2003 | Matsumoto |
| 6,637,437 B1 | 10/2003 | Hungerford et al. |
| 6,638,284 B1 | 10/2003 | Rousseau et al. |
| 6,645,226 B1 | 11/2003 | Jacobs et al. |
| 6,652,594 B2 | 11/2003 | Francis et al. |
| 6,652,595 B1 | 11/2003 | Nicolo |
| 6,653,450 B1 | 11/2003 | Berg et al. |
| 6,656,206 B2 | 12/2003 | Corcoran et al. |
| 6,660,280 B1 | 12/2003 | Allard et al. |
| 6,669,735 B1 | 12/2003 | Pelissier |
| 6,682,760 B2 | 1/2004 | Noff et al. |
| 6,685,714 B2 | 2/2004 | Rousseau |
| 6,706,684 B1 | 3/2004 | Bayon et al. |
| 6,706,690 B2 | 3/2004 | Reich et al. |
| 6,712,859 B2 | 3/2004 | Rousseau et al. |
| 6,719,795 B1 | 4/2004 | Cornwall et al. |
| 6,723,335 B1 | 4/2004 | Moehlenbruck et al. |
| 6,730,299 B1 | 5/2004 | Tayot et al. |
| 6,736,823 B2 | 5/2004 | Darois et al. |
| 6,736,854 B2 | 5/2004 | Vadurro et al. |
| 6,737,371 B1 | 5/2004 | Planck et al. |
| 6,743,435 B2 | 6/2004 | DeVore et al. |
| 6,746,458 B1 | 6/2004 | Cloud |
| 6,752,834 B2 | 6/2004 | Geistlich et al. |
| 6,755,868 B2 | 6/2004 | Rousseau |
| 6,773,723 B1 | 8/2004 | Spiro et al. |
| 6,783,554 B2 | 8/2004 | Amara et al. |
| 6,790,213 B2 | 9/2004 | Cherok et al. |
| 6,790,454 B1 | 9/2004 | Abdul Malak et al. |

(56) References Cited

U.S. PATENT DOCUMENTS

| | | |
|---|---|---|
| 6,800,082 B2 | 10/2004 | Rousseau |
| 6,833,408 B2 | 12/2004 | Sehl et al. |
| 6,835,336 B2 | 12/2004 | Watt |
| 6,852,330 B2 | 2/2005 | Bowman et al. |
| 6,869,938 B1 | 3/2005 | Schwartz et al. |
| 6,872,227 B2 | 3/2005 | Sump et al. |
| 6,893,653 B2 | 5/2005 | Abraham et al. |
| 6,896,904 B2 | 5/2005 | Spiro et al. |
| 6,926,723 B1 | 8/2005 | Mulhauser et al. |
| 6,936,276 B2 | 8/2005 | Spiro et al. |
| 6,939,562 B2 | 9/2005 | Spiro et al. |
| 6,949,625 B2 | 9/2005 | Tayot |
| 6,966,918 B1 | 11/2005 | Schuldt-Hempe et al. |
| 6,971,252 B2 | 12/2005 | Therin et al. |
| 6,974,679 B2 | 12/2005 | Andre et al. |
| 6,974,862 B2 | 12/2005 | Ringeisen et al. |
| 6,977,231 B1 | 12/2005 | Matsuda |
| 6,984,392 B2 | 1/2006 | Bechert et al. |
| 6,988,386 B1 | 1/2006 | Okawa et al. |
| 6,991,643 B2 | 1/2006 | Saadat |
| 7,011,688 B2 | 3/2006 | Gryska et al. |
| 7,021,086 B2 | 4/2006 | Ory et al. |
| 7,022,358 B2 | 4/2006 | Eckmayer et al. |
| 7,025,063 B2 | 4/2006 | Snitkin et al. |
| 7,041,868 B2 | 5/2006 | Greene et al. |
| 7,060,103 B2 | 6/2006 | Carr, Jr. et al. |
| RE39,172 E | 7/2006 | Bayon et al. |
| 7,070,558 B2 | 7/2006 | Gellman et al. |
| 7,087,065 B2 | 8/2006 | Ulmsten et al. |
| 7,094,261 B2 | 8/2006 | Zotti et al. |
| 7,098,315 B2 | 8/2006 | Schaufler |
| 7,101,381 B2 | 9/2006 | Ford et al. |
| 7,115,220 B2 | 10/2006 | Dubson et al. |
| 7,156,804 B2 | 1/2007 | Nicolo |
| 7,156,858 B2 | 1/2007 | Schuldt-Hempe et al. |
| 7,175,852 B2 | 2/2007 | Simmoteit et al. |
| 7,192,604 B2 | 3/2007 | Brown et al. |
| 7,207,962 B2 | 4/2007 | Anand et al. |
| 7,214,765 B2 | 5/2007 | Ringeisen et al. |
| 7,226,611 B2 | 6/2007 | Yura et al. |
| 7,229,453 B2 | 6/2007 | Anderson et al. |
| 7,252,837 B2 | 8/2007 | Guo et al. |
| 7,279,177 B2 | 10/2007 | Looney et al. |
| 7,291,294 B2 | 11/2007 | Stolpe et al. |
| 7,331,199 B2 | 2/2008 | Ory et al. |
| 7,393,319 B2 | 7/2008 | Merade et al. |
| 7,404,199 B2 | 7/2008 | Arneson et al. |
| 7,556,598 B2 | 7/2009 | Rao |
| 7,594,921 B2 | 9/2009 | Browning |
| 7,614,258 B2 | 11/2009 | Cherok et al. |
| 7,615,065 B2 | 11/2009 | Priewe et al. |
| 7,670,380 B2 | 3/2010 | Cauthen, III |
| 7,709,017 B2 | 5/2010 | Tayot |
| 7,718,556 B2 | 5/2010 | Matsuda et al. |
| 7,722,528 B2 | 5/2010 | Arnal et al. |
| 7,732,354 B2 | 6/2010 | Fricke et al. |
| 7,785,334 B2 | 8/2010 | Ford et al. |
| 7,789,888 B2 | 9/2010 | Bartee et al. |
| 7,799,767 B2 | 9/2010 | Lamberti et al. |
| 7,806,905 B2 | 10/2010 | Ford et al. |
| 7,824,420 B2 | 11/2010 | Eldridge et al. |
| 7,828,854 B2 | 11/2010 | Rousseau et al. |
| 7,869,861 B2 | 1/2011 | Moctezuma de la Barrera et al. |
| 7,900,484 B2 | 3/2011 | Cherok et al. |
| 7,931,695 B2 | 4/2011 | Ringeisen |
| 8,048,441 B2 | 11/2011 | Craig et al. |
| 8,100,924 B2 | 1/2012 | Browning |
| 8,123,817 B2 | 2/2012 | Intoccia et al. |
| 8,142,515 B2 | 3/2012 | Therin et al. |
| 8,157,821 B2 | 4/2012 | Browning |
| 8,157,822 B2 | 4/2012 | Browning |
| 8,182,545 B2 | 5/2012 | Cherok et al. |
| 8,197,837 B2 | 6/2012 | Jamiolkowski et al. |
| 8,206,632 B2 | 6/2012 | Rousseau et al. |
| 8,215,310 B2 | 7/2012 | Browning |
| 8,323,675 B2 | 12/2012 | Greenawalt |
| 8,366,787 B2 | 2/2013 | Brown et al. |
| 8,562,633 B2 | 10/2013 | Cully et al. |
| 8,682,052 B2 | 3/2014 | Fitz et al. |
| 8,709,094 B2 | 4/2014 | Stad et al. |
| 8,758,800 B2 | 6/2014 | Stopek et al. |
| 8,834,864 B2 | 9/2014 | Odar et al. |
| 8,846,060 B2 | 9/2014 | Archibald et al. |
| 8,877,233 B2 | 11/2014 | Obermiller et al. |
| 8,945,663 B2 | 2/2015 | Pacetti |
| 8,956,373 B2 | 2/2015 | Ford et al. |
| 9,034,357 B2 | 5/2015 | Stopek |
| 2002/0087174 A1 | 7/2002 | Capello |
| 2002/0095218 A1 | 7/2002 | Carr et al. |
| 2002/0099344 A1 | 7/2002 | Hessel et al. |
| 2002/0131988 A1 | 9/2002 | Foster et al. |
| 2002/0165601 A1 | 11/2002 | Clerc |
| 2003/0086975 A1 | 5/2003 | Ringeisen |
| 2003/0114937 A1 | 6/2003 | Leatherbury et al. |
| 2003/0130745 A1 | 7/2003 | Cherok et al. |
| 2003/0133967 A1 | 7/2003 | Ruszczak et al. |
| 2003/0225355 A1 | 12/2003 | Butler |
| 2004/0034373 A1 | 2/2004 | Schuldt-Hempe et al. |
| 2004/0059356 A1 | 3/2004 | Gingras |
| 2004/0098118 A1 | 5/2004 | Granada et al. |
| 2004/0101546 A1 | 5/2004 | Gorman et al. |
| 2004/0215219 A1 | 10/2004 | Eldridge et al. |
| 2004/0224007 A1 | 11/2004 | Zhang |
| 2005/0002893 A1 | 1/2005 | Goldmann |
| 2005/0021058 A1 | 1/2005 | Negro |
| 2005/0085924 A1 | 4/2005 | Darois et al. |
| 2005/0113849 A1 | 5/2005 | Popadiuk et al. |
| 2005/0137512 A1 | 6/2005 | Campbell et al. |
| 2005/0142161 A1 | 6/2005 | Freeman et al. |
| 2005/0148963 A1 | 7/2005 | Brennan |
| 2005/0175659 A1 | 8/2005 | Macomber et al. |
| 2005/0232979 A1 | 10/2005 | Shoshan |
| 2005/0240261 A1 | 10/2005 | Rakos et al. |
| 2005/0244455 A1 | 11/2005 | Greenawalt |
| 2005/0261782 A1 | 11/2005 | Hoganson |
| 2005/0267521 A1 | 12/2005 | Forsberg |
| 2005/0288691 A1 | 12/2005 | Leiboff |
| 2006/0025785 A1 | 2/2006 | Cully et al. |
| 2006/0034887 A1 | 2/2006 | Pelissier |
| 2006/0116696 A1 | 6/2006 | Odermatt et al. |
| 2006/0121078 A1 | 6/2006 | Trogolo et al. |
| 2006/0135921 A1 | 6/2006 | Wiercinski et al. |
| 2006/0147501 A1 | 7/2006 | Hillas et al. |
| 2006/0188546 A1 | 8/2006 | Giroux |
| 2006/0216320 A1 | 9/2006 | Kitazono et al. |
| 2006/0224038 A1 | 10/2006 | Rao |
| 2006/0252981 A1 | 11/2006 | Matsuda et al. |
| 2006/0253203 A1 | 11/2006 | Alvarado |
| 2006/0282103 A1 | 12/2006 | Fricke et al. |
| 2007/0088391 A1 | 4/2007 | McAlexander et al. |
| 2007/0129736 A1 | 6/2007 | Solecki |
| 2007/0198040 A1 | 8/2007 | Buevich et al. |
| 2007/0244548 A1 | 10/2007 | Myers et al. |
| 2007/0260268 A1 | 11/2007 | Bartee et al. |
| 2007/0299538 A1 | 12/2007 | Roeber |
| 2008/0017200 A1 | 1/2008 | Carepa et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0147200 A1 | 6/2008 | Rousseau et al. |
| 2008/0161837 A1 | 7/2008 | Toso et al. |
| 2008/0172071 A1 | 7/2008 | Barker |
| 2008/0199506 A1 | 8/2008 | Horres et al. |
| 2008/0255593 A1 | 10/2008 | St-Germain |
| 2009/0035341 A1 | 2/2009 | Wagener et al. |
| 2009/0036995 A1 | 2/2009 | Lozier et al. |
| 2009/0036996 A1 | 2/2009 | Roeber |
| 2009/0069826 A1 | 3/2009 | Walther et al. |
| 2009/0082792 A1 | 3/2009 | Koyfman et al. |
| 2009/0105526 A1 | 4/2009 | Piroli Torelli et al. |
| 2009/0125107 A1 | 5/2009 | Maxwell |
| 2009/0142385 A1 | 6/2009 | Gross et al. |
| 2009/0163936 A1 | 6/2009 | Yang et al. |
| 2009/0171377 A1 | 7/2009 | Intoccia et al. |

(56) References Cited

U.S. PATENT DOCUMENTS

| | | |
|---|---|---|
| 2009/0187197 A1 | 7/2009 | Roeber et al. |
| 2009/0192530 A1 | 7/2009 | Adzich et al. |
| 2009/0198260 A1 | 8/2009 | Ford et al. |
| 2009/0216338 A1 | 8/2009 | Gingras et al. |
| 2009/0270999 A1 | 10/2009 | Brown |
| 2009/0276057 A1 | 11/2009 | Trabucco et al. |
| 2009/0281558 A1 | 11/2009 | Li |
| 2009/0299538 A1 | 12/2009 | Suzuki |
| 2009/0326676 A1 | 12/2009 | Dupic et al. |
| 2010/0003308 A1 | 1/2010 | Tapolsky et al. |
| 2010/0089409 A1 | 4/2010 | Bertagnoli |
| 2010/0094404 A1 | 4/2010 | Greenhalgh et al. |
| 2010/0104608 A1 | 4/2010 | Abuzaina et al. |
| 2010/0160375 A1 | 6/2010 | King |
| 2010/0286716 A1 | 11/2010 | Ford et al. |
| 2010/0312043 A1 | 12/2010 | Goddard |
| 2010/0318108 A1 | 12/2010 | Datta et al. |
| 2011/0082330 A1 | 4/2011 | Deitch |
| 2011/0144667 A1 | 6/2011 | Horton et al. |
| 2011/0238094 A1 | 9/2011 | Thomas et al. |
| 2011/0251699 A1 | 10/2011 | Ladet |
| 2011/0257666 A1 | 10/2011 | Ladet et al. |
| 2011/0264120 A1 | 10/2011 | Bayon et al. |
| 2011/0265283 A1 | 11/2011 | Duncan |
| 2011/0293688 A1 | 12/2011 | Bennett et al. |
| 2011/0320009 A1 | 12/2011 | Ladet et al. |
| 2012/0010637 A1 | 1/2012 | Stopek et al. |
| 2012/0016388 A1 | 1/2012 | Houard et al. |
| 2012/0029537 A1 | 2/2012 | Mortarino |
| 2012/0029540 A1 | 2/2012 | Adams |
| 2012/0053602 A1 | 3/2012 | Adzich et al. |
| 2012/0065727 A1 | 3/2012 | Reneker et al. |
| 2012/0082712 A1 | 4/2012 | Stopek et al. |
| 2012/0109165 A1 | 5/2012 | Mathisen et al. |
| 2012/0116423 A1 | 5/2012 | Gleiman et al. |
| 2012/0116425 A1 | 5/2012 | Intoccia et al. |
| 2012/0150204 A1 | 6/2012 | Mortarino et al. |
| 2012/0179175 A1 | 7/2012 | Hammell |
| 2012/0179176 A1 | 7/2012 | Wilson et al. |
| 2012/0239063 A1 | 9/2012 | Lee |
| 2012/0259348 A1 | 10/2012 | Paul |
| 2013/0060263 A1 | 3/2013 | Bailly et al. |

FOREIGN PATENT DOCUMENTS

| | | |
|---|---|---|
| CN | 201879864 U | 6/2011 |
| DE | 19544162 C1 | 4/1997 |
| DE | 19718903 A1 | 12/1997 |
| DE | 19636961 A1 | 3/1998 |
| DE | 19751733 A1 | 12/1998 |
| DE | 19832634 A1 | 1/2000 |
| DE | 101 20 942 A1 | 10/2001 |
| DE | 10019604 A1 | 10/2001 |
| DE | 10043396 C1 | 6/2002 |
| EP | 0194192 A1 | 9/1986 |
| EP | 0248544 A1 | 12/1987 |
| EP | 0263360 A2 | 4/1988 |
| EP | 0276890 A2 | 8/1988 |
| EP | 0372969 A1 | 6/1990 |
| EP | 0531742 A1 | 3/1993 |
| EP | 544485 A1 | 6/1993 |
| EP | 0552576 A1 | 7/1993 |
| EP | 0611561 A1 | 8/1994 |
| EP | 614650 A2 | 9/1994 |
| EP | 0621014 A1 | 10/1994 |
| EP | 0625891 A1 | 11/1994 |
| EP | 0637452 A1 | 2/1995 |
| EP | 0664132 A1 | 7/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 0800791 A1 | 10/1997 |
| EP | 827724 A2 | 3/1998 |
| EP | 0836838 A1 | 4/1998 |
| EP | 0847727 A1 | 6/1998 |
| EP | 03876808 A1 | 11/1998 |
| EP | 0895762 A2 | 2/1999 |
| EP | 898944 A2 | 3/1999 |
| EP | 1017415 A1 | 7/2000 |
| EP | 1036545 A2 | 9/2000 |
| EP | 1052319 A1 | 11/2000 |
| EP | 1055757 A1 | 11/2000 |
| EP | 1090590 A2 | 4/2001 |
| EP | 1158082 A2 | 11/2001 |
| EP | 1 216 717 A1 | 6/2002 |
| EP | 1 216 718 A1 | 6/2002 |
| EP | 0693523 B1 | 11/2002 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1645232 A1 | 4/2006 |
| EP | 1674048 A1 | 6/2006 |
| EP | 1691606 A1 | 8/2006 |
| EP | 1782848 A2 | 5/2007 |
| EP | 2016956 A2 | 1/2009 |
| EP | 2314254 A2 | 4/2011 |
| EP | 2353545 A1 | 8/2011 |
| EP | 2404571 A1 | 1/2012 |
| FR | 2244853 A1 | 4/1975 |
| FR | 2257262 A1 | 8/1975 |
| FR | 2 308 349 A1 | 11/1976 |
| FR | 2453231 A1 | 10/1980 |
| FR | 2601371 A1 | 1/1988 |
| FR | 2612392 A1 | 9/1988 |
| FR | 2715309 A1 | 7/1995 |
| FR | 2715405 A1 | 7/1995 |
| FR | 2 724 563 A1 | 3/1996 |
| FR | 2730406 A1 | 8/1996 |
| FR | 2744906 A1 | 8/1997 |
| FR | 2766698 A1 | 2/1999 |
| FR | 2771622 A1 | 6/1999 |
| FR | 2773057 A1 | 7/1999 |
| FR | 2774277 A1 | 8/1999 |
| FR | 2779937 A1 | 12/1999 |
| FR | 2857851 A1 | 1/2005 |
| FR | 2859624 A1 | 3/2005 |
| FR | 2863277 A1 | 6/2005 |
| FR | 2876020 A1 | 4/2006 |
| FR | 2884706 A1 | 10/2006 |
| FR | 2924330 A1 | 6/2009 |
| FR | 2929834 A1 | 10/2009 |
| FR | 2949687 A1 | 3/2011 |
| FR | 2949688 A1 | 3/2011 |
| FR | 2 951 069 A1 | 4/2011 |
| FR | 2951069 A1 | 4/2011 |
| FR | 2 953 709 A1 | 6/2011 |
| FR | 2953709 A1 | 6/2011 |
| GB | 1174814 A | 12/1969 |
| GB | 2 051 153 A | 1/1981 |
| GB | 2306110 A | 4/1997 |
| JP | H0332677 A | 2/1991 |
| JP | H05237128 A | 9/1993 |
| JP | H09137380 A | 5/1997 |
| JP | 2010-508121 A | 3/2010 |
| WO | 89/02445 A1 | 3/1989 |
| WO | 89/08467 A1 | 9/1989 |
| WO | 90/12551 A1 | 11/1990 |
| WO | 92/06639 A2 | 4/1992 |
| WO | 92/20349 A1 | 11/1992 |
| WO | 9311805 A1 | 6/1993 |
| WO | 93/18174 A1 | 9/1993 |
| WO | 94/17747 A1 | 8/1994 |
| WO | 95/07666 A1 | 3/1995 |
| WO | 95/18638 A1 | 7/1995 |
| WO | 95/32687 A1 | 12/1995 |
| WO | 96/03091 A1 | 2/1996 |
| WO | 96/08277 A1 | 3/1996 |
| WO | 96/09795 A1 | 4/1996 |
| WO | 96/14805 A1 | 5/1996 |
| WO | 96/41588 A1 | 12/1996 |
| WO | 97/35533 A1 | 10/1997 |
| WO | 9806355 A1 | 2/1998 |

(56) References Cited

FOREIGN PATENT DOCUMENTS

| | | |
|---|---|---|
| WO | 98/35632 A1 | 8/1998 |
| WO | 98/49967 A1 | 11/1998 |
| WO | 99/05990 A1 | 2/1999 |
| WO | 99/06079 A1 | 2/1999 |
| WO | 99/06080 A1 | 2/1999 |
| WO | 9951163 A1 | 10/1999 |
| WO | 00/16821 A1 | 3/2000 |
| WO | 00/67663 A1 | 11/2000 |
| WO | 01/15625 A1 | 3/2001 |
| WO | 01/80773 A1 | 11/2001 |
| WO | 0180788 A2 | 11/2001 |
| WO | 0181667 A1 | 11/2001 |
| WO | 02/07648 A1 | 1/2002 |
| WO | 0217853 A2 | 3/2002 |
| WO | 0234304 A1 | 5/2002 |
| WO | 02/078568 A1 | 10/2002 |
| WO | 03/002168 A1 | 1/2003 |
| WO | 03007847 A1 | 1/2003 |
| WO | 2004004600 A1 | 1/2004 |
| WO | 2004071349 A2 | 8/2004 |
| WO | 2004078120 A2 | 9/2004 |
| WO | 2004103212 A1 | 12/2004 |
| WO | 2005011280 A1 | 2/2005 |
| WO | 2005013863 A2 | 2/2005 |
| WO | 2005018698 A1 | 3/2005 |
| WO | 2005028581 A1 | 3/2005 |
| WO | 2005048708 A1 | 6/2005 |
| WO | 2005105172 A1 | 11/2005 |
| WO | 2006018552 A1 | 2/2006 |
| WO | 2006020922 A2 | 2/2006 |
| WO | 2006023444 A2 | 3/2006 |
| WO | 2006/040760 A2 | 4/2006 |
| WO | 2006036967 A1 | 4/2006 |
| WO | 2006040760 A2 | 4/2006 |
| WO | 2006102374 A2 | 9/2006 |
| WO | 2007025266 A2 | 3/2007 |
| WO | 2007048099 A2 | 4/2007 |
| WO | 2008127411 A1 | 10/2008 |
| WO | 2009031035 A2 | 3/2009 |
| WO | 2009071998 A2 | 6/2009 |
| WO | 2009075786 A1 | 6/2009 |
| WO | 2010043978 A2 | 4/2010 |
| WO | 2010043979 A2 | 4/2010 |
| WO | 2010043980 A2 | 4/2010 |
| WO | 2010093333 A1 | 8/2010 |
| WO | 2010129641 A1 | 11/2010 |
| WO | 2011007062 A1 | 1/2011 |
| WO | 2011038740 A1 | 4/2011 |
| WO | 2011117758 A2 | 9/2011 |
| WO | 2013098343 A1 | 7/2013 |

OTHER PUBLICATIONS

International Search Report issued in corresponding application No. PCT/EP2012/062671, mailed Sep. 3, 2012.
Ellouali, M. et al., "Antitumor Activity of Low Molecular Weight Fucans Extracted from Brown Seaweed Ascophyllum Nodosum," Anticancer Res., Nov.-Dec. 1993, pp. 2011-2020, 12 (6A).
Malette, W. G. et al., "Chitosan, A New Hemostatic," Ann Th. Surg., Jul. 1983, pp. 55-58, 36.
Langenbech, M. R. et al., "Comparison of biomaterials in the early postoperative period," Surg Endosc., May 2003, pp. 1105-1109, 17 (7).
Bracco, P. et al., "Comparison of polypropylene and polyethylene terephthalate (Dacron) meshes for abdominal wall hernia repair: A chemical and morphological study," Hernia, 2005, pp. 51-55, 9 (1), published online Sep. 2004.
Klinge, U. et al., "Foreign Body Reaction to Meshes Used for the Repair of Abdominal Wall Hernias," Eur J. Surg, Sep. 1999, pp. 665-673, 165.
Logeart, D. et al., "Fucans, sulfated polysaccharides extracted from brown seaweeds, inhibit vascular smooth muscle cell proliferation. II. Degradation and molecular weight effect," Eur. J. Cell. Biol., Dec. 1997, pp. 385-390, 74(4).
Haneji, K. et al., "Fucoidan extracted from Cladosiphon Okamuranus Tokida Induces Apoptosis of Human T-cell Leukemia Virus Type 1-Infected T-Cell Lines and Primary Adult T-Cell Leukemia Cells," Nutrition and Cancer, 2005, pp. 189-201, 52(2), published online Nov. 2009.
Junge, K. et al., "Functional and Morphologic Properties of a Modified Mesh for Inguinal Hernia Repair," World J. Surg., Sep. 2002, pp. 1472-1480, 26.
Klinge, U. et al., "Functional and Morphological Evaluation of a Low-Weight, Monofilament Polypropylene Mesh for Hernia Repair," J. Biomed. Mater. Res., Jan. 2002, pp. 129-136, 63.
Welty, G. et al., "Functional impairment and complaints following incisional hernia repair with different polypropylene meshes," Hernia, Aug. 2001; pp. 142-147, 5.
Varum, K. et al., "In vitro degradation rates of partially N-acetylated chitosans in human serum," Carbohydrate Research, Mar. 1997, pp. 99-101, 299.
Haroun-Bouhedja, F. et al., "In Vitro Effects of Fucans on MDA-MB231 Tumor Cell Adhesion and Invasion," Anticancer Res., Jul.-Aug. 2002, pp. 2285-2292, 22(4).
Scheidbach, H. et al., "In vivo studies comparing the biocompatibility of various polypropylene meshes and their handling properties during endoscopic total extraperitoneal (TEP) patchplasty: An experimental study in pigs," Surg. Enclose., Feb. 2004, pp. 211-220,18(2).
Blondin, C. et al., "Inhibition of Complement Activation by Natural Sulfated Polysaccharides (Fucans) from Brown Seaweed," Molecular Immuol., Mar. 1994, pp. 247-253, 31(4).
Zvyagintseva, T. et al., "Inhibition of complement activation by water-soluble polysaccharides of some far-eastern brown seaweeds," Comparative Biochem and Physiol, Jul. 2000, pp. 209-215,126(3).
Rosen, M. et al., "Laparoscopic component separation in the single-stage treatment of infected abdominal wall prosthetic removal," Hernia, 2007, pp. 435-440, 11, published online Jul. 2007.
Amid, P., "Lichtenstein tension-free hernioplasty: Its inception, evolution, and principles," Hernia, 2004; pp. 1-7, 8, published online Sep. 2003.
Boisson-Vidal, C. et al., "Neoangiogenesis Induced by Progenitor Endothelial Cells: Effect of Fucoidan From Marine Algae," Cardiovascular & Hematological Agents in Medicinal Chem., Jan. 2007, pp. 67-77, 5(1).
O'Dwyer, P. et al., "Randomized clinical trial assessing impact of a lightweight or heavyweight mesh on chronic pain after inguinal hernia repair," Br. J. Surg., Feb. 2005, pp. 166-170, 92(2).
Muzzarelli, R. et al., "Reconstruction of parodontal tissue with chitosan," Biomaterials, Nov. 1989, pp. 598-604, 10.
Haroun-Bouhedja, F. et al., "Relationship between sulfate groups and biological activities of fucans," Thrombosis Res., Dec. 2000, pp. 453-459, 100(5).
Blondin, C. et al., "Relationships between chemical characteristics and anticomplementary activity of fucans," Biomaterials, Mar. 1996, pp. 597-603, 17(6).
Strand, S. et al., "Screening of Chitosans and Conditions for Bacterial Flocculation," Biomacromolecules, Mar. 2001, 126-133, 2.
Kanabar, V. et al., "Some structural determinants of the antiproliferative effect of heparin-like molecules on human airway smooth muscle," Br. J. Pharmacol., Oct. 2005, pp. 370-777, 146(3).
Hirano, S. et al., "The blood biocompatibility of chitosan and N-acylchitosans," J. Biomed. Mater. Res., Apr. 1985, 413-417, 19.
Rao, B. et al., "Use of chitosan as a biomaterial: Studies on its safety and hemostatic potential," J. Biomed. Mater. Res., Jan. 1997, pp. 21-28, 34.
Prokop, A. et al., "Water Soluble Polymers for Immunoisolation I: Complex Coacevation and Cytotoxicity," Advances in Polymer Science, Jul. 1998, pp. 1-51, 136.
Collins, R. et al., "Use of collagen film as a dural substitute: Preliminary animal studies," Journal of Biomedical Materials Research, Feb. 1991, pp. 267-276, vol. 25.
Preliminary Search Report from French Patent Office dated Dec. 20, 2006, 3 pages.

(56) References Cited

OTHER PUBLICATIONS

Japanese Office Action mailed May 2, 2016 in corresponding Japanese Patent Application No. 2014-519493, together with English translation, 7 pages.
Australian Office Action issued Apr. 13, 2016 in corresponding Australian Patent Application No. 2012283292, 3 pages.

UMBILICAL HERNIA PROSTHESIS

The present invention provides a prosthesis, for repairing hernias, for example, comprising a mesh and a member for reinforcing the mesh.

In humans the abdominal wall consists of fat and muscles interconnected by aponeuroses. A break in continuity may occur at the level of the aponeuroses, allowing part of the peritoneum to pass through and form a sac, known as a hernia, containing either fat or a portion of the intestine. Hernias or ventral ruptures (hernias occurring on a parietal surgical scar) are manifested by a protrusion on the surface of the skin and are called umbilical or inguinal hernias or ventral ruptures, for example, as a function of their location.

To repair a hernia, surgeons often fit a synthetic mesh prosthesis that replaces or reinforces the weakened anatomical tissue.

However, the efficacy of the prosthesis, and thus minimizing the risk of relapse, depend to a great degree on the proper fixing of the prosthesis. In particular, before being fixed, the prosthesis must be correctly spread over the abdominal wall that it is intended to reinforce. Prostheses of mesh type, i.e. based on an arrangement of threads forming a textile, are generally flexible, and to introduce them into the hernia they are often folded to reduce their volume. They therefore tend to form creases on the abdominal wall when they are introduced onto the implantation site. In this respect spreading them out is of primary importance but may prove difficult, in particular in the case of treating an umbilical hernia, which, being smaller than an inguinal hernia, offers little working space and little visibility for manipulation of the prosthesis by the surgeon.

In the case of umbilical hernias, for example, or when the aim of treatment is to repair trocart holes or preventive, the size of the defect to be treated is small, for example from 1 to 4 cm diameter, and open surgery may be envisaged without widening the defect. However, in this type of surgery, the surgeon has little working space and little visibility. It would thus be preferable to have a prosthesis that is easy to position, to spread out and to fix, if possible avoiding the necessity for sutures at the periphery of the prosthesis, which is complicated and laborious under such working conditions.

Failure to spread the prosthesis out perfectly against the abdominal wall leads to the risk of trapping the peritoneal sac and the risk of insertion of a soft organ between the prosthesis and the abdominal wall, which can lead to the risk of adhesions, pain and intestinal blockage and increase the possibility of relapse. It is therefore essential for the surgeon to be sure that no part of the prosthesis remains folded and that no viscera or any part of the intestines lie between the prosthesis and the abdominal wall. Moreover, incorrect positioning of the sutures or incorrect fixing of the prosthesis risks distortion of the prosthesis and the creation of tensions.

Thus in the case of an umbilical hernia in particular, having a small orifice for introducing the prosthesis, it would be beneficial to have a prosthesis adapted to occupy a small volume in a first configuration in order to facilitate its introduction into the abdominal cavity via said orifice and then to be deployed, spread out and pressed easily against the abdominal wall so that the surgeon is sure of the optimal positioning of the prosthesis and can moreover fix the prosthesis efficaciously without sutures at its periphery, and this, despite the little intrinsic visibility of small size hernias.

Various prostheses that may be folded up and then deployed are available.

The present invention concerns a prosthesis that is adapted to be folded up in order to reduce the volume that it occupies at the time of its introduction into a small incision and on the other hand to be spread out and fixed easily so that the surgeon is sure of the perfect spreading of the prosthesis and that it may be fixed efficaciously at a certain distance between the centre of the prosthesis and its periphery without sutures at the periphery of the prosthesis and this, despite the little intrinsic visibility of small size hernias.

The prosthesis of the invention is beneficial for treating hernias of the abdominal wall, in particular for treating umbilical hernias where the defect is small.

A first aspect of the present invention provides a prosthesis comprising:
  at least one flexible mesh delimited by a peripheral exterior edge,
  at least two tongues extending from one face of the mesh, and
  at least one member for reinforcing said mesh, characterized in that said reinforcing member takes the form of a frame fastened to said mesh and substantially adopting the shape of said peripheral exterior edge of the mesh, said frame being set back from said peripheral exterior edge and being provided with two hinge points, the line passing through said two hinge points also passing through the centre of the mesh and thus forming a line for folding the mesh in two.

The reinforcing member or frame may be rigid or have some flexibility. According to the present invention, the mesh and thus the prosthesis can be folded in two because of the presence of the two hinge points of the frame, regardless of the presence or not of intrinsic elastic properties of the frame.

In the context of the present application the term "mesh" refers to an arrangement of biocompatible threads, for example a knitted, woven or non-woven material, preferably of the openwork kind, i.e. having pores encouraging tissue recolonization. Such a mesh may be bioresorbable, partly bioresorbable or permanent. It is sufficiently flexible to be folded up at the time of its introduction into the abdominal cavity. The mesh may be produced from one layer of textile or from a plurality of layers of textiles. Such meshes are well known to the person skilled in the art. The mesh usable for the invention may be supplied in any shape (rectangular, square, circular, oval, etc.) and then cut to match the shape of the hernia defect. For example, the mesh may have the overall shape of a disc or an oval: in this case the frame also has a circular or oval shape and is preferably in the form of a ring. Alternatively, the mesh may have a globally square or rectangular shape: in this case the frame also has a square or rectangular shape. The frame is set back from the exterior peripheral edge of the mesh: thus, whilst adopting the shape of the contour of the mesh, the frame has an exterior perimeter smaller than that of the exterior peripheral edge of the mesh: in other words, the exterior peripheral edge of the mesh extends a certain distance beyond the frame. This distance may be greater than or equal to 1 mm, for example. In other words also, the frame and the exterior peripheral edge of the mesh are of similar geometric shape but the frame shows dimensions which are less than that of the exterior peripheral edge of the mesh.

As will become apparent from the following description, the shape of the frame and its location, set back slightly from the exterior peripheral edge of the mesh, enable the surgeon, when implanting the prosthesis, to fix it to the peritoneum efficaciously without requiring sutures at the periphery of the mesh: the surgeon is able to fix the prosthesis along the interior contour of the frame only, said interior contour defining a stitches fixing line: this avoids the surgeon having to apply stitches to the prosthesis at the exterior peripheral edge of the mesh, which is difficult to reach and hardly visible because of the small size of the incision. The interior contour of the frame of the prosthesis of the invention defines a fixing line, or stitching line, located approximately half way between the centre of the mesh and its exterior peripheral edge, along which the surgeon may locate the stitches when he fixes the prosthesis to the abdominal wall. Nevertheless, perfect spreading out of the prosthesis is assured by the presence of the frame which, by adopting the shape of the contour of the exterior peripheral edge, ensures deployment of the prosthesis and pressing thereof onto the abdominal wall.

In one embodiment of the invention, the mesh is a knitted fabric: because of the stitches that form it, a knitted fabric makes it possible to obtain openwork faces encouraging cellular recolonization after implantation. The knitted fabric may be a two-dimensional knitted fabric or a three-dimensional knitted fabric.

In the context of the present application, the expression "two-dimensional knitted fabric" means a knitted fabric having two opposite faces linked together by stitches but having no spacers imparting a certain thickness to it: such a knitted fabric may be obtained, for example, by knitting threads on a warp or Raschel knitting machine using two guide bars. Examples of two-dimensional knitted fabrics suitable for the present invention are given in the document WO2009/071998.

In the present application, the expression "three-dimensional knitted fabric" means a knitted fabric having two opposite faces linked together by spacers imparting a significant thickness to the knitted fabric, said spacers consisting of connecting threads additional to the threads forming the two faces of the knitted fabric. Such a knitted fabric may be obtained, for example, using a double-bed Raschel knitting machine or warp knitting machine with a plurality of guide bars. Examples of knitting three-dimensional knitted fabrics suitable for the present invention are given in the documents WO99/05990, WO2009/031035, WO2009/071998.

In one embodiment, said frame is set back from the exterior peripheral edge and is of serpentine shape, forming undulations. For example, said frame is in the form of a flat ribbon forming undulations substantially in the plane of said mesh. As will become apparent from the description given hereinafter, this configuration of the frame makes it possible, when fixing the prosthesis to the biological tissue, to execute a suture in the prosthesis at a given location without deforming the prosthesis as a whole during this operation; deformation of the prosthesis caused by the suture at the given location is smoothed out by the undulating frame. Thus the frame and therefore the rest of the prosthesis remain correctly positioned, and in particular remain pressed against the abdominal wall, during the fixing of the prosthesis. In addition, the frame preferably possesses a certain rigidity along its section.

In one embodiment, said reinforcing member is produced in bioresorbable material. Thus the reinforcing member fulfils its role of stiffening the prosthesis during positioning and implantation of the prosthesis and is then degraded progressively once the mesh is recolonized by the surrounding cells.

The bioresorbable material may be chosen, for example, from polylactic acid (PLA), polycaprolactone (PCL), polydioxanone (PDO), trimethylene carbonate (TMC), polyvinyl alcohol (PVA), polyhydroxyalkanoate (PHA), oxidized cellulose, polyglycol acid (PGA), copolymers of these materials and mixtures thereof.

Alternatively, the reinforcing member is produced in a non-bioresorbable material chosen from polypropylene, a polyester such as polyethylene terephthalate, polyamide, silicone, polyetheretherketone (PEEK), polyaryletheretherketone (PAEK) and mixtures thereof.

In another embodiment, said reinforcing member is produced from a combination of bioresorbable material and non-bioresorbable material.

In one embodiment, said tongues have a globally rectangular shape and are provided at one of their ends with a widened part by which they are fixed to said mesh. As will become apparent from the description given hereinafter, the tongues are useful to the surgeon by facilitating positioning of the prosthesis at the centre of the defect to be treated and for fixing the prosthesis to the biological tissue.

In one embodiment of the invention, said tongues are textile tongues. The textile of the tongues may be identical to that of the mesh or different. The tongues may be made of bioresorbable material or not. A suitable bioresorbable material for the manufacturing of the tongues may be selected from bioresorbable materials mentioned above for the reinforcing member.

In one embodiment of the invention, the widened part being separate from the rest of the tongue, said widened part is produced in gripping textile and can thus be attached to and/or detached from the rest of the tongue at will. Examples of production of gripping textile are described in the document WO0181667.

For example, the widened part of the tongues may be sewn to said mesh. The widened part enables better fixing of the tongues to the mesh. In one embodiment, the widened part of the tongues is fixed to the mesh by means of the reinforcing member.

In one embodiment of the invention, said two tongues are fixed on either side of said folding line, preferably at two places symmetrical about this folding line.

In one embodiment of the invention said mesh has the shape of a disc, said frame being substantially in the form of a circular ring, and said tongues are fixed to two diametrically opposed places on said ring, said two places being spaced by 90° from each of said two hinge points. The face of the mesh including said two tongues may be provided with two additional tongues fixed to the mesh at the locations of the two hinge points of the ring.

In one embodiment of the invention, at least a portion of the tongues is of a colour different from that of the mesh: for example, the widened parts of the tongues may be of a colour different from that of the mesh. Indeed, the colour difference between the widened parts of the tongues, or the whole tongues, and the mesh is particularly advantageous in view of the little visibility offered by the small size of the working area: this colour difference allows defining a line, said line pointing out to the surgeon where to complete the stitches for fixing the prosthesis to the abdominal wall.

In embodiments, said mesh being disc-shaped and said frame being substantially in the form of a circular ring, said prosthesis comprises four of said tongues, the widened parts of which being of a colour different from that of the mesh, said four widened parts being distributed along an interior contour of said ring, symmetrically with respect to said folding line M, two of said widened parts on one side of said folding line M, the other two of said widened parts on the other side of said folding line M.

In embodiments, all four widened parts are under the form of isosceles triangles of textile, each triangle being fixed to said mesh via its base, all four triangles showing identical elongation and tensile strength properties in the centripetal direction.

For example, each isosceles triangle is fixed to the mesh via its base by means of the ring, the rectangular part of the tongue being attached to the vertex angle of the isosceles triangle. Because of the four isosceles triangles of textile having the same mechanical properties in the centripetal direction, when the surgeon pulls on the rectangular parts of the four tongues at the time he puts the prosthesis in place and fixes it to the abdominal wall, all widened parts of the tongues react similarly and the traction exerted by the surgeon on the whole prosthesis via the four tongues is regularly distributed. The prosthesis is therefore properly positioned. In addition, because the four isosceles triangles of textile have a colour different from that of the mesh, the surgeon readily identifies the stitching line as defined above and the step of fixing the prosthesis to the abdominal wall is facilitated. As will appear from the description below, the method of manufacturing a prosthesis with four widened parts under the form of four isosceles triangle of textile having identical mechanical properties is simple and easy.

In one embodiment of the invention, the free ends of the tongues are joined together by a centring thread. Such a configuration enables the surgeon to use the centring thread to position and fix the prosthesis particularly easily and effectively when implanting the prosthesis, as will become apparent from the description given below.

In one embodiment of the invention, the face of the mesh opposite that including said tongues is covered with a non-adherent coating.

Such a coating makes it possible in particular to avoid the formation of unwanted severe post-operative fibrous adhesions.

In the context of the present application the expression "non-adherent" refers to a non-porous, smooth, biocompatible coating or material offering no space for cellular recolonization and preferably encouraging the birth of a peritoneum.

Figure 2:
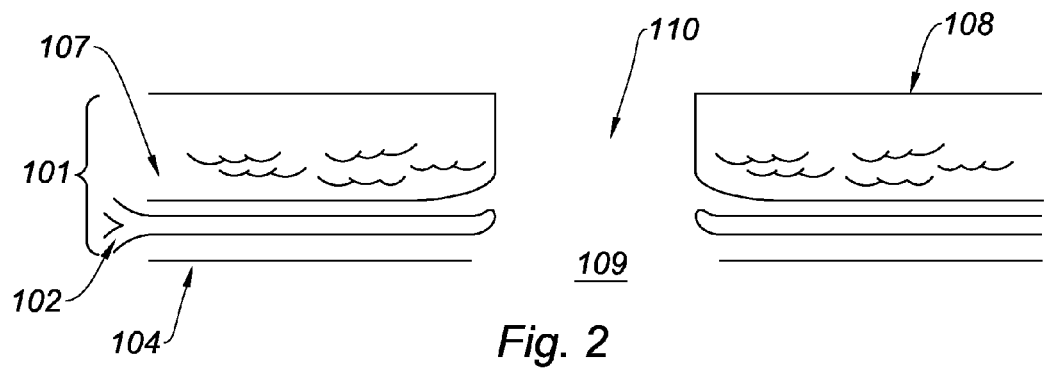
Figure 3:
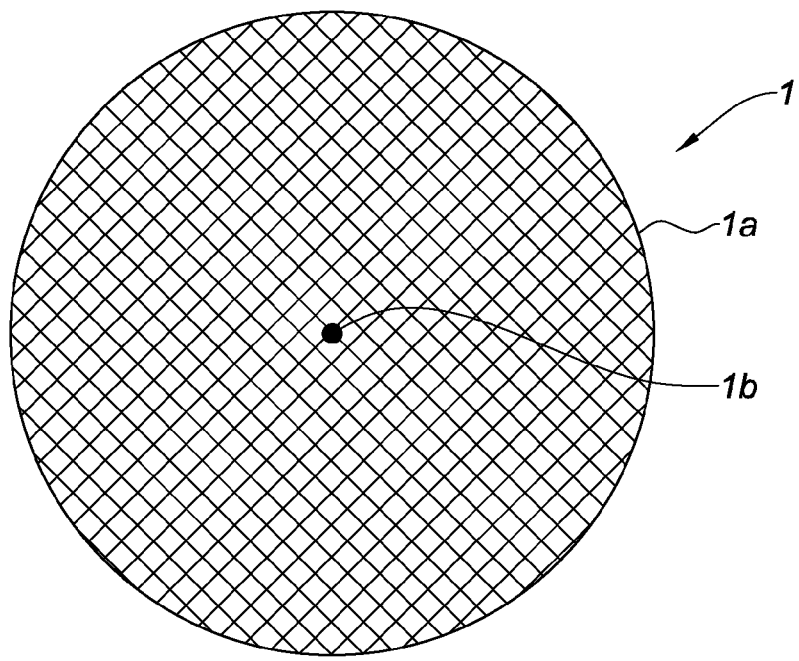
Figure 4:
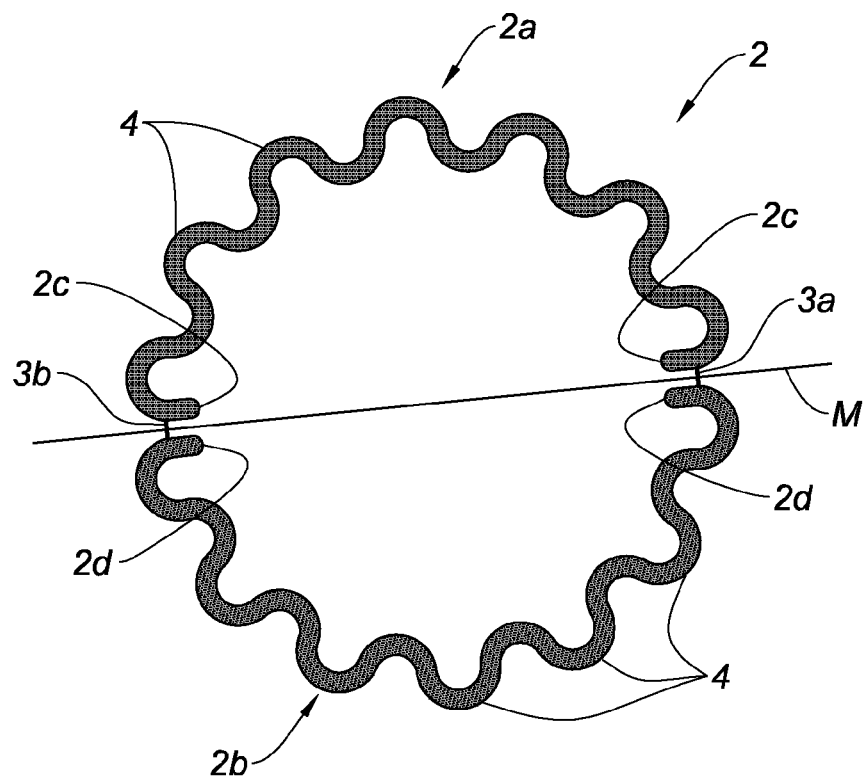
Figure 5:
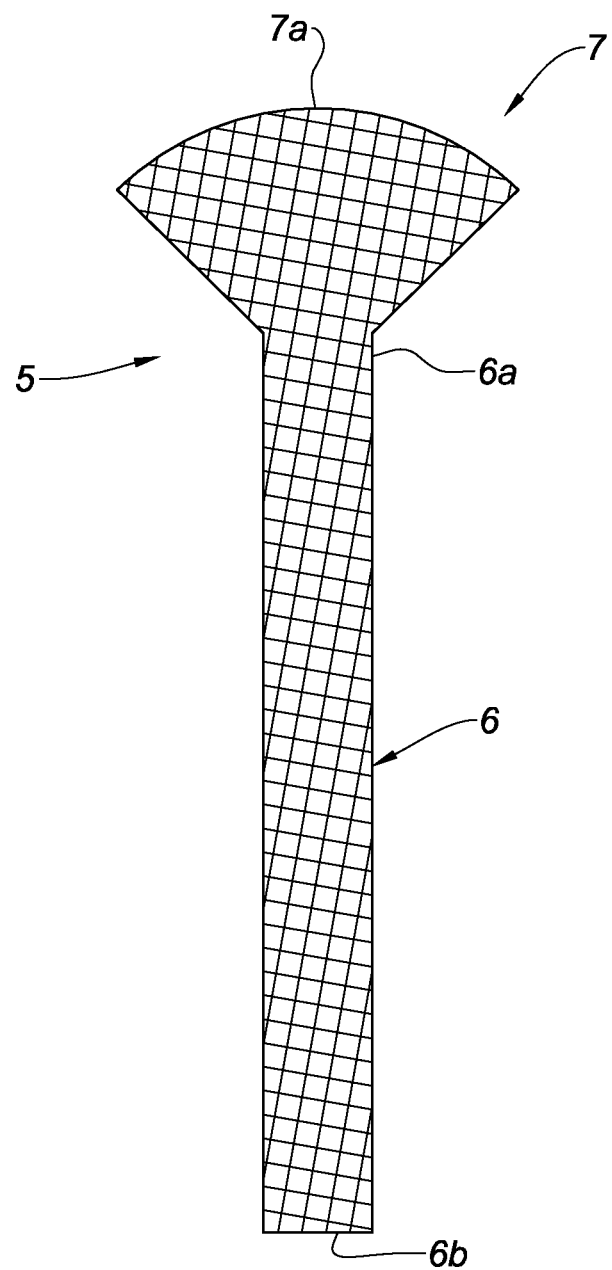
Figure 6:
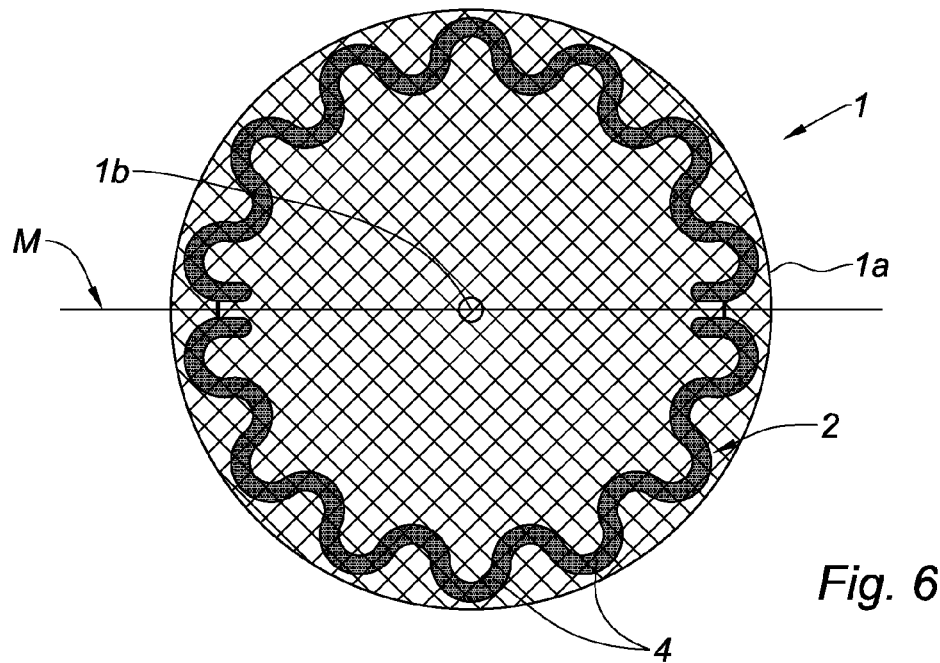
Figure 7A:
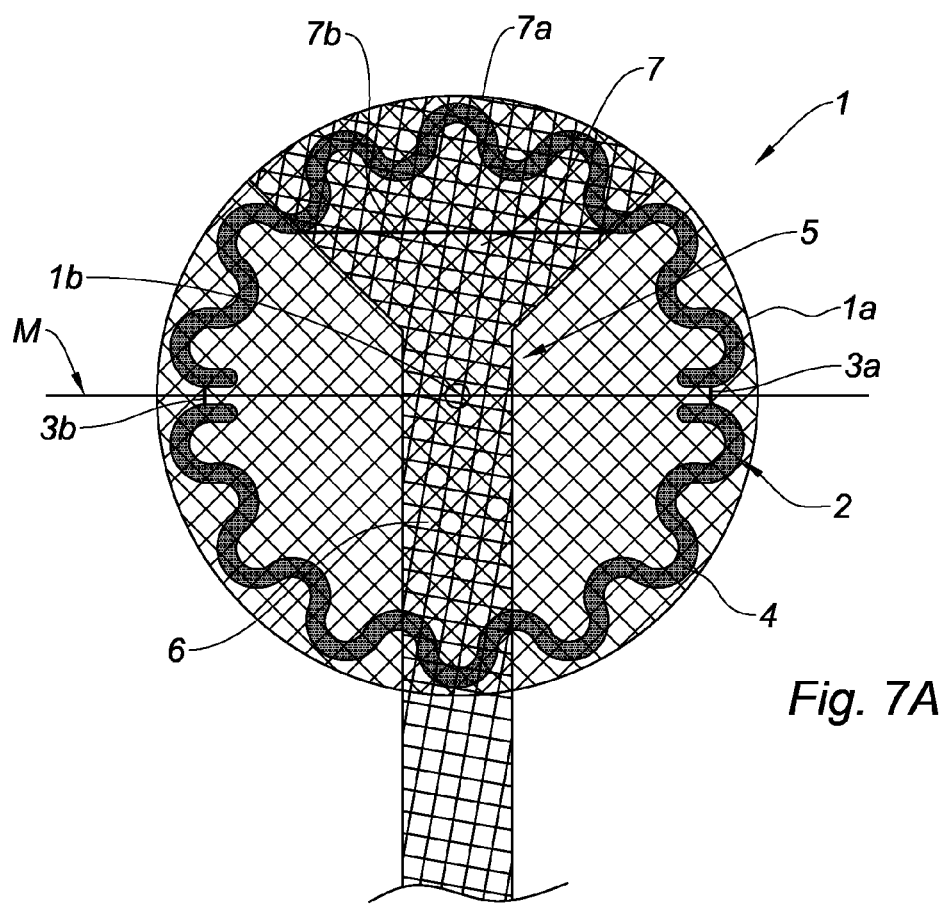
Figure 7B:
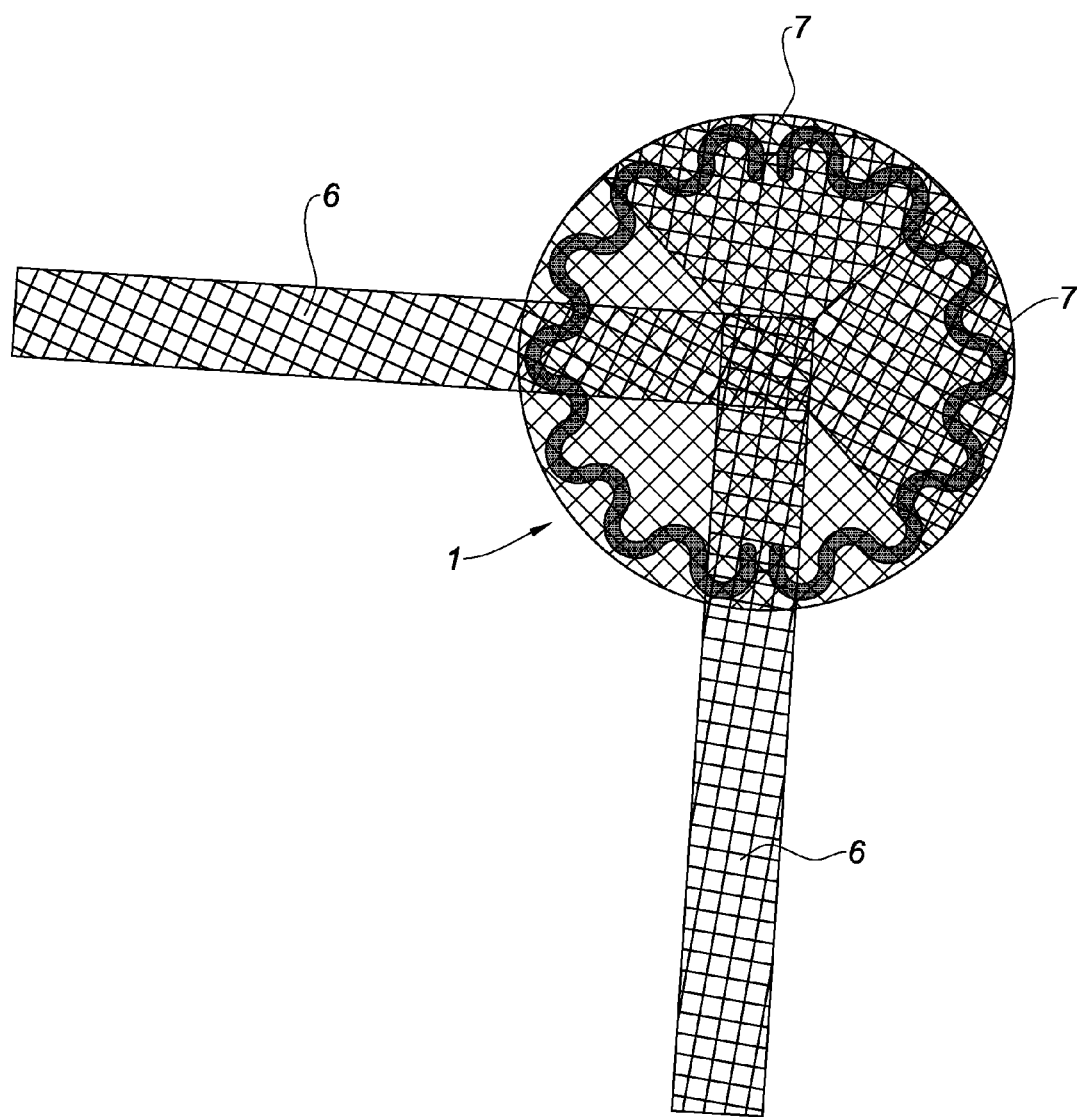
Figure 8A:
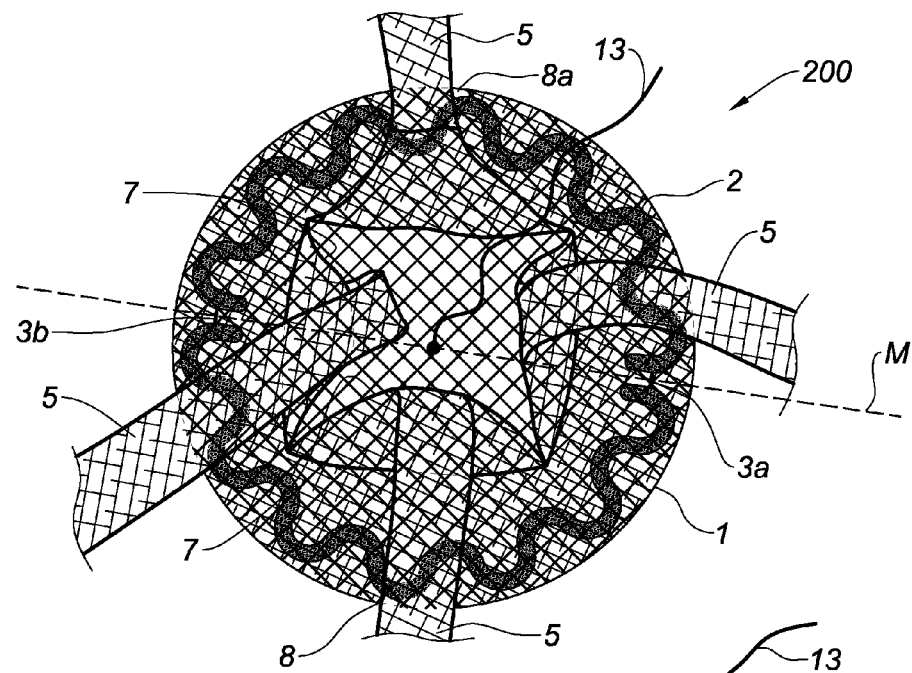
Figure 9:
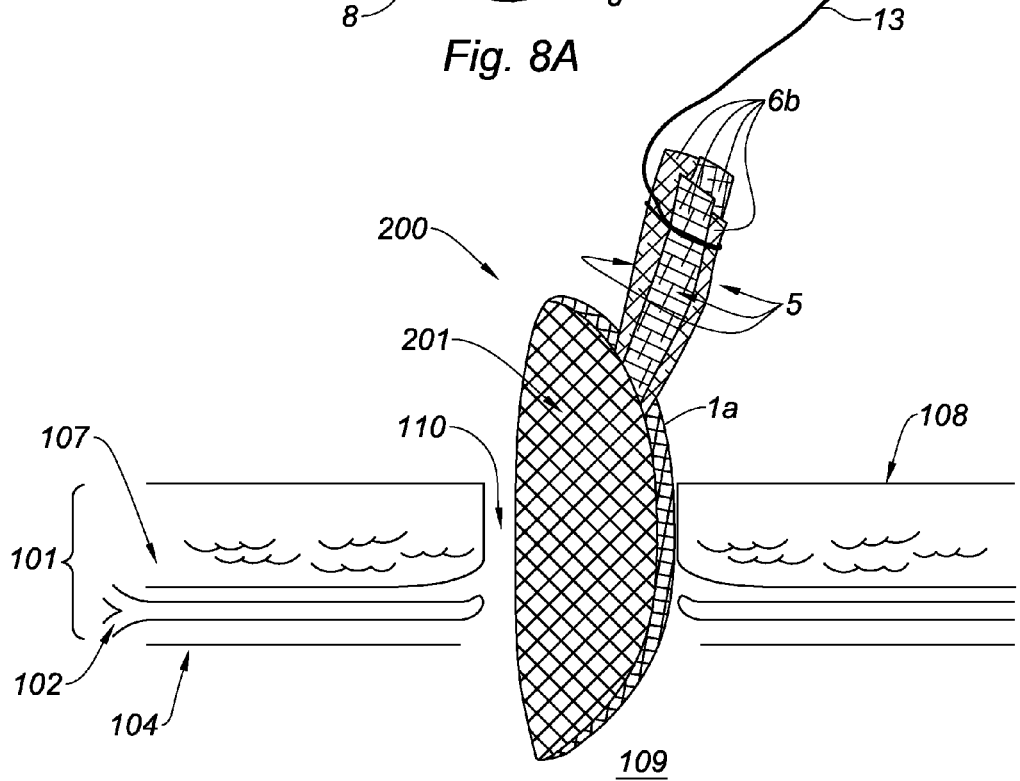
Figure 8B:
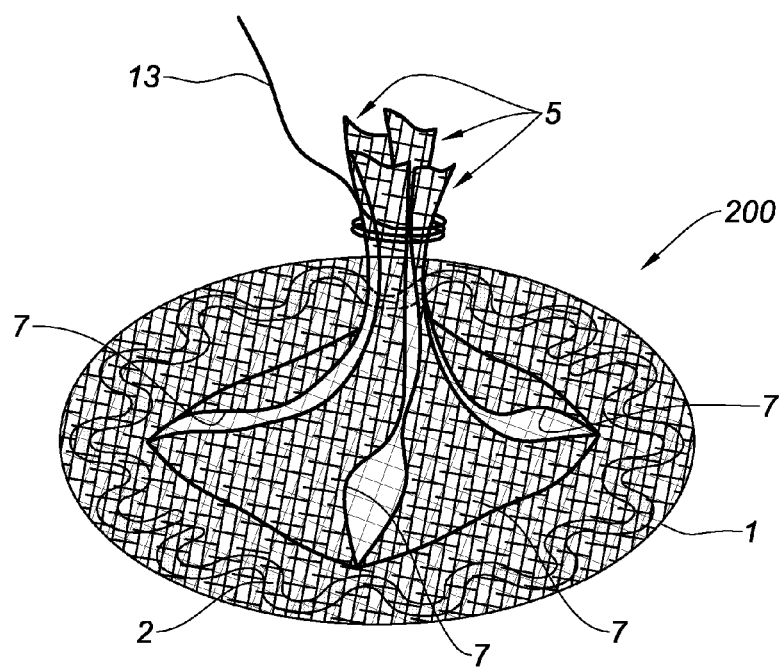
Figure 11:
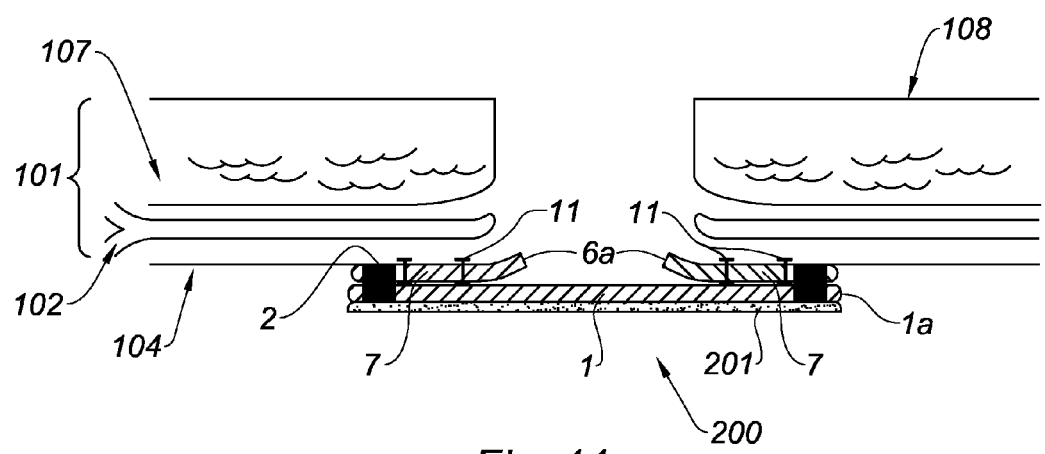
Figure 10A:
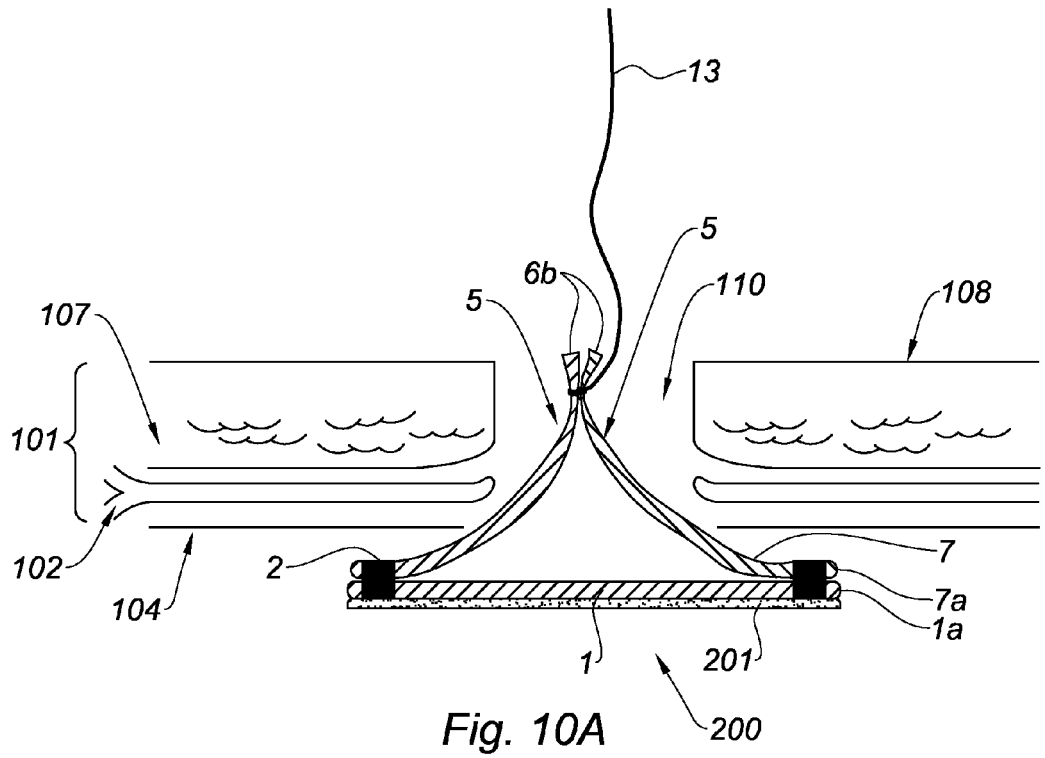
Figure 10B:
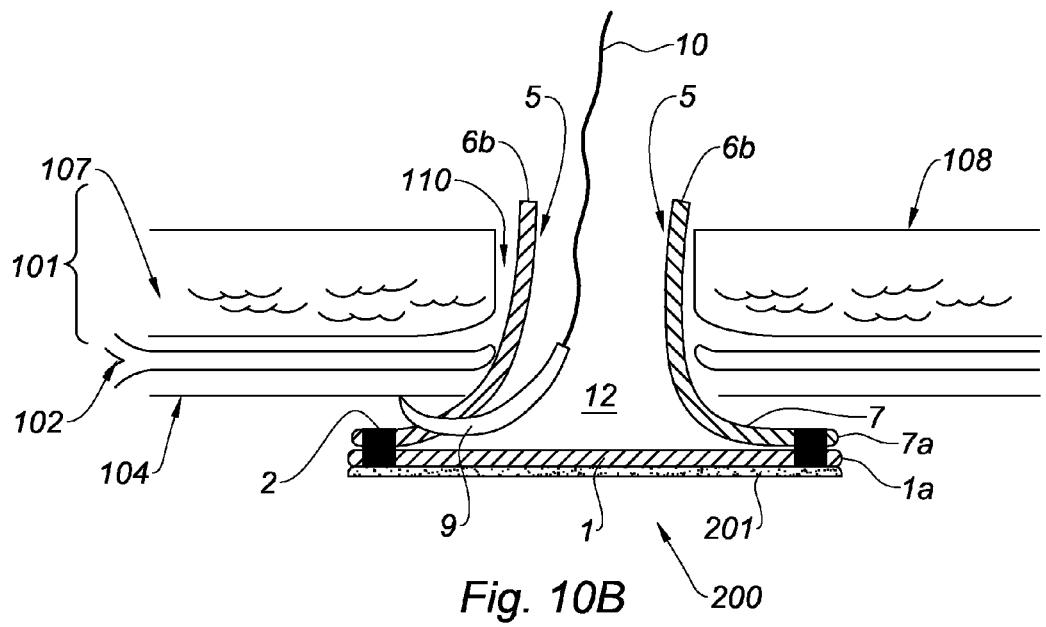
Figure 12:
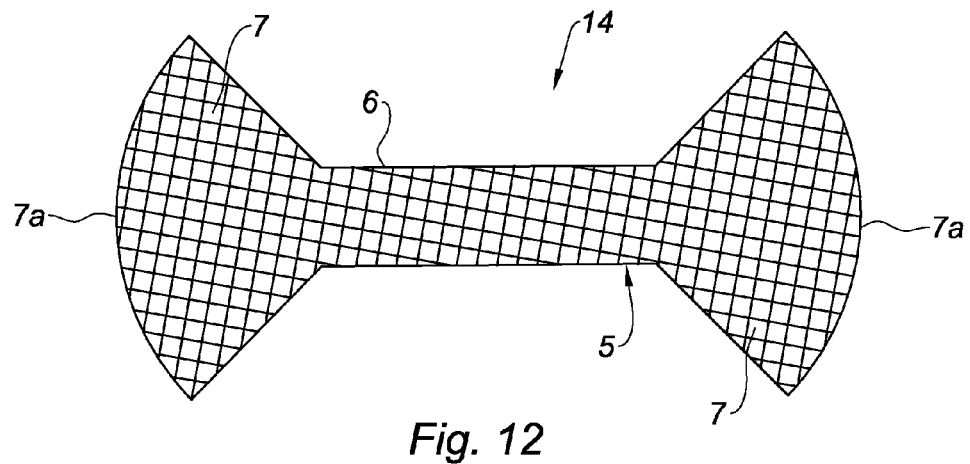
Figure 13:
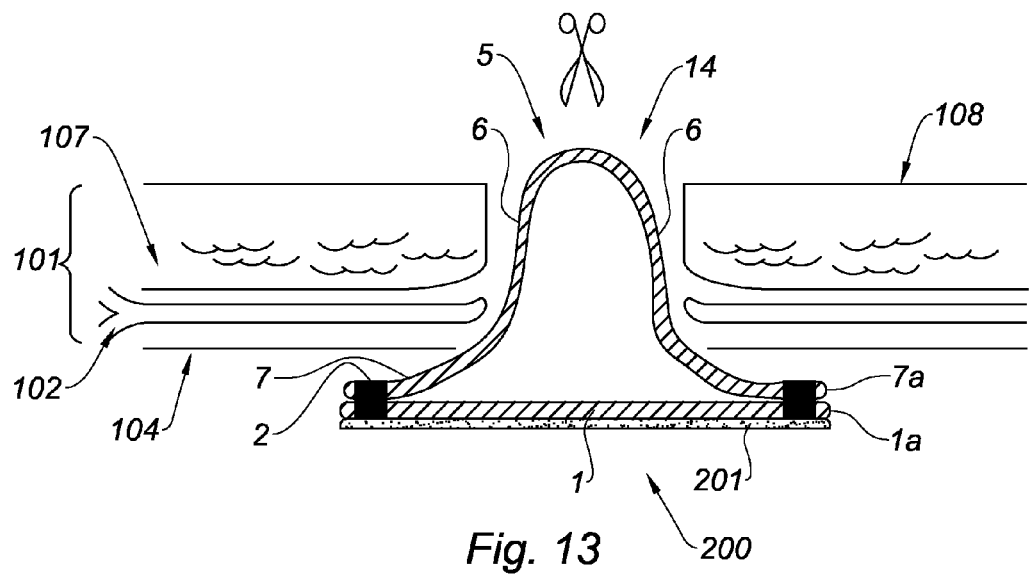

The present invention will emerge more clearly from the description given hereinafter and from the appended drawings, in which:

FIG. 1 is a representation in section of a median abdominal hernia or ventral rupture, FIG. 2 is a simplified view of the hernia from FIG. 1 after the surgeon has made an abdominal incision and removed the hernia sac, FIG. 3 is a top view of one embodiment of a mesh for a prosthesis of the invention, FIG. 4 is a top view of a reinforcing member for the prosthesis of the invention, FIG. 5 is a top view of a tongue of the prosthesis of the invention, FIG. 6 is a top view of the mesh and the reinforcing member of the prosthesis of the invention, FIG. 7A is a top view of the mesh, the reinforcing member and a tongue of the prosthesis of the invention, FIG. 7B is a view of the prosthesis from FIG. 7A when a second tongue has been fitted, FIG. 8A is a top view of the prosthesis of the invention, FIG. 8B is a perspective view of a variant of the prosthesis of the invention, FIG. 9 is a simplified sectional view of the introduction of the prosthesis from FIG. 8B into the hernia defect, FIG. 10A is a simplified sectional view of the positioning of the prosthesis from FIG. 8B after deployment thereof at the implantation site, FIG. 10B is a simplified sectional view of the fixing of the prosthesis from FIG. 8B, FIG. 11 is a view in section of the prosthesis from FIG. 8B when fixed to the biological tissues just before closure of the abdominal incision by the surgeon, FIG. 12 is a top view of an embodiment of the prosthesis of the invention with two tongues, FIG. 13 is a simplified sectional view of the placement of a prosthesis of the invention using the tongues from FIG. 12, FIGS. 14-17 are top views showing the successive steps of a method for manufacturing a prosthesis of the invention comprising four widened parts of textile having identical mechanical properties.

FIG. 1 represents a hernia defect 100 of the abdominal wall 101 that is characterized by a break in the continuity of the aponeurosis 102 surrounding the straight muscles 103 and a passage through the peritoneum 104 forming a sac, the hernia sac 105, that contains either fat (epiploon) or part of the viscera 106, and which then presses on the fatty tissues 107 and is flush with the skin 108. One treatment of a hernia defect 100 entails replacing and retaining the viscera 106 in the abdominal cavity 109.

FIG. 2 shows the hernia defect 100 from FIG. 1 after the surgeon has made an incision in the skin 108, the abdominal wall 101 and the peritoneum 104 and has reduced the hernia sac. The viscera are not shown in FIG. 2: they have been pushed back into the abdominal cavity 109. The surgeon must now introduce into the abdominal cavity 109, via the incision 110 that has been made, a prosthesis for reinforcing the abdominal wall, before closing the incision 110 by means of sutures, for example. In the case of an umbilical hernia, the size of the incision 110 is particularly small, for example of the order of 1 to 4 cm diameter.

FIG. 3 represents a mesh 1 in the form of a disc usable with the reinforcing member from FIG. 4 and tongues such as that from FIG. 5 to produce a prosthesis of the invention.

The mesh 1 is made from a knitted, woven or non-woven arrangement of biocompatible threads. It may be bioresorbable, partly bioresorbable or permanent. The mesh is generally openwork, incorporating pores for better tissue integration. This mesh 1 is sufficiently flexible to be folded when the prosthesis is introduced into the abdominal cavity 109 via the incision 110. However, the mesh is generally a textile having no elasticity enabling it to return to a spread out configuration of its own accord after it has been folded up. The mesh 1 may be produced from a textile layer or a plurality of textile layers. The textile may be a two-dimensional or three-dimensional knitted fabric. Such meshes are well known to the person skilled in the art and are not described in more detail here. The mesh may be supplied in the form of a strip that is cut to the dimensions of the defect to be treated. In the example represented, the mesh 1 has the shape of a disc adapted to the shape of the incision 110 at the hernia defect 100 and delimited by an exterior peripheral edge 1a. In other embodiments, the mesh may be of oval shape. Alternatively, the mesh may be of rectangular or square shape.

FIG. 4 represents a reinforcing member of a prosthesis of the invention, suitable for the shape of the mesh 1 from FIG. 3: as is apparent from FIG. 4 and FIG. 6, the reinforcing member takes the form of a frame 2 substantially adopting the shape of the exterior peripheral edge 1a of the mesh 1. Thus the overall shape of the frame 2 is a circular ring. The frame 2 is provided with two hinge points 3a and 3b that are diametrically opposite in the example shown. The two hinge points (3a, 3b) make it possible to fold the frame 2, for example when force is applied by the surgeon, resulting in two globally identical parts. The hinge points (3a, 3b) preferably do not have any elasticity of their own: thus, once folded in two, the frame 2 can be unfolded only by the action of an external force, for example exerted by the surgeon.

The frame 2 thus consists of two parts, namely two semicircles 2a and 2b, connected together by two hinge points (3a, 3b). As seen in FIG. 4, the respective ends (2c; 2d) of the semicircles 2a and 2b are blunted or rounded to prevent trauma when implanting the prosthesis. In the example shown, the two semicircles 2a and 2b are symmetrical: the two hinge points (3a; 3b) define a median line M passing through the centre of the circle delimited by the frame and also through the centre of the mesh 1 when the frame 2 is fixed to the mesh 1, as shown in FIG. 6. Thus the mesh 1 may be folded in two even when fitted with the frame 2: consequently, as will become apparent in the remainder of the description, the prosthesis may be folded. Similarly, given the configuration of the frame 2 in two parts and the absence of any elasticity of the frame 2 and its hinge points (3a, 3b), the prosthesis is able to adopt only two configurations: either a flat and spread out configuration or a folded in two configuration. As explained later, the fact that the prosthesis can adopt only two configurations facilitates the task of the surgeon, who can immediately determine if the prosthesis is in its spread out configuration or not.

As seen in FIGS. 4 and 6, the frame 2 is an undulating ring set back from the exterior peripheral edge 1a, consisting of undulations 4. Referring to FIG. 6 in particular, the exterior peripheral edge 1a of the mesh extends some distance beyond the exterior contour of the frame 2: this distance may be greater than or equal to 1 mm, for example. As will become apparent from the description given hereinafter, the location of the frame 2, slightly set back from the exterior peripheral edge 1a, facilitates efficacious fixing of the prosthesis to the abdominal wall, in particular in an area located more or less half way between the centre and the edge of the mesh.

The undulations 4 of the frame 2 may be regular or not. In particular, in the example shown, the frame 2 is in the form of a flat ribbon of material forming undulations 4 in the plane of the frame 2, which is substantially the plane of the prosthesis. As will become apparent in the remainder of the description, such a shape imparts to the frame 2 great flexibility in the plane of the frame 2 and thus in the plane of the prosthesis: it is thus possible to suture part of the prosthesis at a given place, without rocking or deforming the prosthesis as a whole: the deformation created at the location of the suture is smoothed out by the undulations 4 of the frame 2 over the whole of the periphery of the prosthesis. In addition, the frame 2 shows a rigidity along its section, so that it neither deforms radially in the outward nor in the inward directions.

Materials suitable for producing the reinforcing member of the prosthesis of the invention may be any biocompatible materials having some rigidity so as to respond to the expectations disclosed above.

The frame 2 can thus be produced in any biocompatible material, bioresorbable or not. In a preferred embodiment, it is made in bioresorbable material. In the present application, the term "bioresorbable" refers to the characteristic whereby a material is absorbed by biological tissues and disappears in vivo after a given period, which may vary from one day to several months, for example, depending on the chemical nature of the material.

Bioresorbable materials suitable for the fabrication of the reinforcing member of the prosthesis of the present invention include polylactic acid (PLA), polycaprolactone (PCL), polydioxanone (PDO), trimethylene carbonate (TMC), polyvinyl alcohol (PVA), polyhydroxyalkanoate (PHA), oxidized cellulose, polyglycolic acid (PGA), copolymers of these materials and mixtures thereof. Bioresorbable materials suitable for the fabrication of the reinforcing member of the prosthesis of the invention include polyester (glycolid, dioxanone, trimethylene carbonate) available from the company Covidien under the trade name "BIOSYN®" and polyester (glycolid, caprolactone, trimethylene carbonate, lactid) available commercially from the company Covidien under the trade name "CAPROSYN®".

Non-bioresorbable materials suitable for the fabrication of the reinforcing member of the prosthesis of the present invention include polypropylene, polyesters such as polyethylene terephthalate, polyamide, silicone, polyetheretherketone (PEEK), polyaryletheretherketone (PAEK) and mixtures thereof.

Each part of the reinforcing member of the prosthesis of the invention may be made in one piece, for example, by injection moulding one or more biocompatible thermoplastic or thermosetting materials. The hinge points (3a, 3b) of the frame 2 may be produced in the same material as the rest of the frame: these hinge points (3a, 3b) take the form for example of very thin bridges of material in order to enable folding of the frame 2 without causing separation of the two parts joined together by these bridges.

FIG. 5 shows a tongue 5 suitable for the prosthesis of the invention. As may be seen in this figure, the tongue 5 has a globally rectangular part 6 and a widened part 7 situated at one end 6a of the rectangular part 6, said end 6a forming a junction between the rectangular part 6 and the widened part 7. In this figure, the widened part 7 has a trapezoidal overall shape with a circular arc base 7a: as may be seen in FIGS. 7A and 7B, the widened part 7 of each tongue 5 is intended to be fixed to the mesh 1, for example by means of the frame 2. Alternatively or in addition, the widened part 7 of the tongue 5 may be sewn to the mesh along a seam 7b as shown in FIG. 7A.

The free end 6b of the rectangular part 6 may be joined to the free ends of the other tongues 5, as shown in FIG. 8B. The free ends 6b of the tongues may be joined during fabrication of the prosthesis or at the time of implantation by the surgeon. Thus the length of the rectangular part 6 must be sufficient to enable joining of the tongues 5: nevertheless, this length must not be too great in order not to impede the surgeon at the time of implanting the prosthesis. The length of the rectangular part 6 is preferably from 2 to 6 cm and more preferably from 2 to 4 cm.

In the embodiment shown on FIG. 5, the tongue 5 is made in one piece. In other embodiments described below with respect to FIGS. 14-17, the widened part and the rectangular part may be two separate parts that are assembled before use. In such a case, the two parts may be in different materials.

The tongue 5 may be produced in any biocompatible material imparting to it the flexibility necessary for it to be picked up by the surgeon during fitting of the prosthesis, as described hereinafter. The tongues 5 are intended to assist the surgeon to position the prosthesis relative to the hernia and then to fix it to the abdominal wall.

For example, the tongue 5 is in textile. This textile may be identical to that forming the mesh 1 or different. In an embodiment in which the widened part and the rectangular part are two initially separate parts, the widened part for example may consist of a gripping textile as described in WO0181667 and the rectangular part may consist of an openwork textile stuck to the widened part.

The tongues may be realized in a bioresorbable material, for example such as that described above for the reinforcing member.

FIG. 8A shows a prosthesis 200 of the invention made with the mesh 1 from FIG. 3, the frame 2 from FIG. 4 and four tongues 5 from FIG. 5.

In an embodiment of the invention that is not shown, the prosthesis of the invention has only two tongues: in such a case, the two tongues are preferably fixed on either side of the folding line M, for example by means of the reinforcing member.

In the embodiment shown in FIG. 8A, the four tongues 5 are arranged symmetrically around the ring formed by the frame 2 in order to balance each other. In particular, two of the tongues 5 are fixed to two diametrically opposite places 8 and 8a of the frame 2, said two places being each spaced by 90° from the hinge points 3a and 3b. Two other tongues 5 are fixed at the locations of the two hinge points 3a and 3b. Each tongue 5 is fixed to the mesh 1 by its widened part 7, the circular arc parts of the widened parts of the tongues 5 being adjacent in pairs. The centre 1b of the mesh 1 is moreover provided with a centring thread 13. This centring thread is intended to be grasped by the surgeon when fitting the prosthesis 200 on the implantation site. The centring thread 13 is long enough to enable the surgeon to manipulate it outside the body of the patient with the prosthesis 200 inside the body of the patient. The presence of the four tongues 5, regularly distributed as described above, and the centring thread 13 enables the surgeon to balance the tension between the various tongues at the time of positioning the prosthesis and to centre the latter prosthesis better relative to the defect to be closed.

In one embodiment of the prosthesis 200 the reinforcing member, namely the frame 2 in the example shown, is welded directly to the mesh 1 and to the circular arc parts 7a of the four tongues 5. Thus the frame 2 is fastened both to the mesh 1 and to the widened parts 7 of the tongues 5. The prosthesis 200 is thus substantially contained in a plane comprising the mesh 1, the frame 2 and the widened parts 7 of the tongues 5.

In another embodiment of the invention, shown in FIG. 8B, the centring thread 13 is not fixed to the centre of the mesh 1 but joins the free ends 6b of the four tongues 5. This centring thread 13 may then be placed by the surgeon before implanting the prosthesis 200. In this embodiment, the centring thread 13 may pass through the tongues 5 or simply surround them to hold them together without passing through them.

In the FIG. 8B embodiment, the face of the mesh 1 opposite that including the tongues 5 is covered by a non-adherent coating 201. Such a non-adherent coating makes it possible to avoid in particular the formation of unwanted severe post-operative fibrous adhesions; once the prosthesis 200 has been implanted, the face of the prosthesis 200 covered by the non-adherent coating 201 faces the abdominal cavity 109.

The non-adherent coating or material is chosen from bioresorbable materials, non-bioresorbable materials and mixtures thereof. The non-bioresorbable non-adherent materials may be chosen from polytetrafluoroethylene, polyethylene glycol, polysiloxane, polyurethane, and mixtures thereof.

Said non-adherent coating or material is preferably bioresorbable: bioresorbable materials suitable for said non-adherent coating may be chosen from collagen, oxidized cellulose, polyacrylate, trimethylene carbonate, caprolactone, dioxanone, glycolic acid, lactic acid, glycolide, lactide, polysaccaride, for example chitosan, polyglucuronic acid, hyaluronic acid, dextran and mixtures thereof.

The non-adherent coating makes it possible to protect the mesh 1 of the prosthesis 200 at least during the initial scar formation phase, i.e. the mesh 1 is not exposed to inflammatory cells, such as granulocytes, monocytes, macrophages or the giant multinucleated cells generally activated by surgery. At least during the initial scar formation phase, the duration of which may vary from about 5 days to about 10 days, only the non-adherent coating is accessible to the various factors such as proteins, enzymes, cytokines or inflammatory cells.

If the non-adherent coating consists of non-resorbable materials, it thus protects the mesh 1 before and after implantation and throughout the duration of implantation of the prosthesis 200.

Moreover, thanks to the non-adherent coating, surrounding fragile tissues, such as the hollow viscera, for example, are protected, in particular from unwanted severe post-operative fibrous adhesion.

If the non-adherent material includes a bioresorbable material, it is preferable to choose a bioresorbable material that is not resorbed in less than a few days in order for the non-adherent coating to be able to fulfil its function of protecting the intestine and hollow organs during the days following surgery until cellular rehabilitation of the prosthesis takes over protecting these fragile organs.

Because of its two-part reinforcing member, namely the frame 2 consisting of the two semicircles 2a and 2b in the example shown, connected together by hinge points 3a, 3b, the prosthesis 200 of the invention may adopt a folded configuration after the surgeon folds it along the folding line M. Thus to implant the prosthesis 200 the surgeon folds it in two so that it occupies a smaller volume, which facilitates introduction of the prosthesis into the hernia defect 100 (see FIG. 2) by the surgeon.

The mesh 1 and the non-adherent coating 201 are sufficiently flexible to follow successive deformations of the prosthesis 200 as the latter is introduced to the implantation site.

FIGS. 14-17 describe various steps of a method for manufacturing an embodiment of a prosthesis 210 of the invention made with the mesh 1 of FIG. 3, the frame 2 of FIG. 4 and four widened parts 207, made separately from the rectangular parts of the tongues. For clarity's sake, the rectangular parts of the tongues are not shown on FIGS. 14-17: these rectangular parts are similar to the rectangular part 6 of tongue 5 of FIG. 5 and may be either integrate with the widened parts 217 or else attached to said widened parts 217 by any fixation means such as sewing, welding, gluing or by means of a gripping textile.

As will appear from the description below, the four widened parts 217 of prosthesis 210 are arranged symmetrically along the interior contour of the ring formed by the frame 2, and they all have the same mechanical properties.

The manufacturing process of such embodiments will now be described with reference to FIGS. 14-17.

Figure 14:
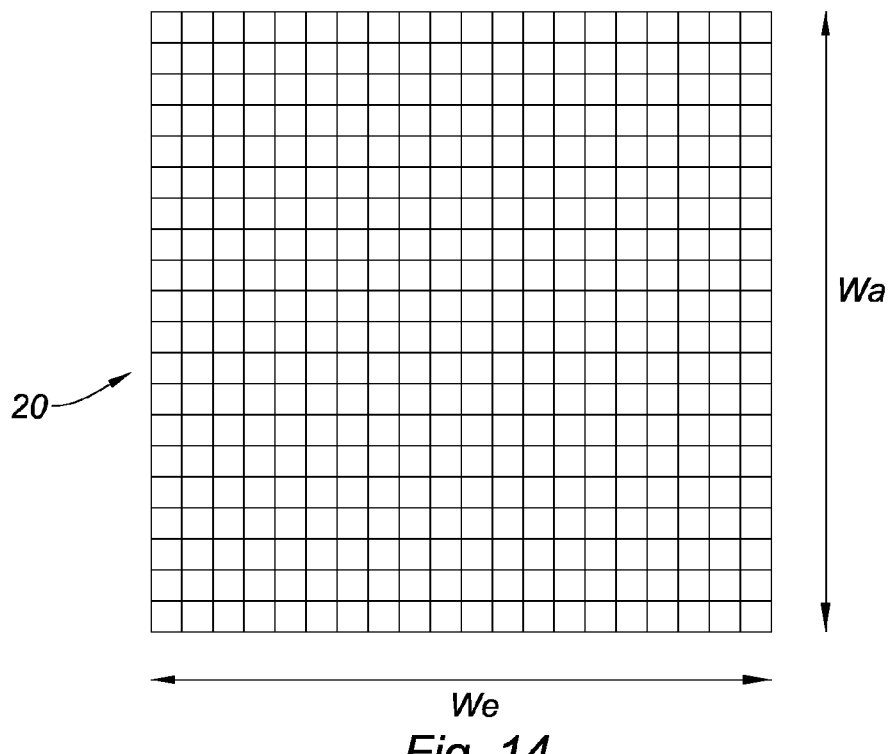
Figure 17:
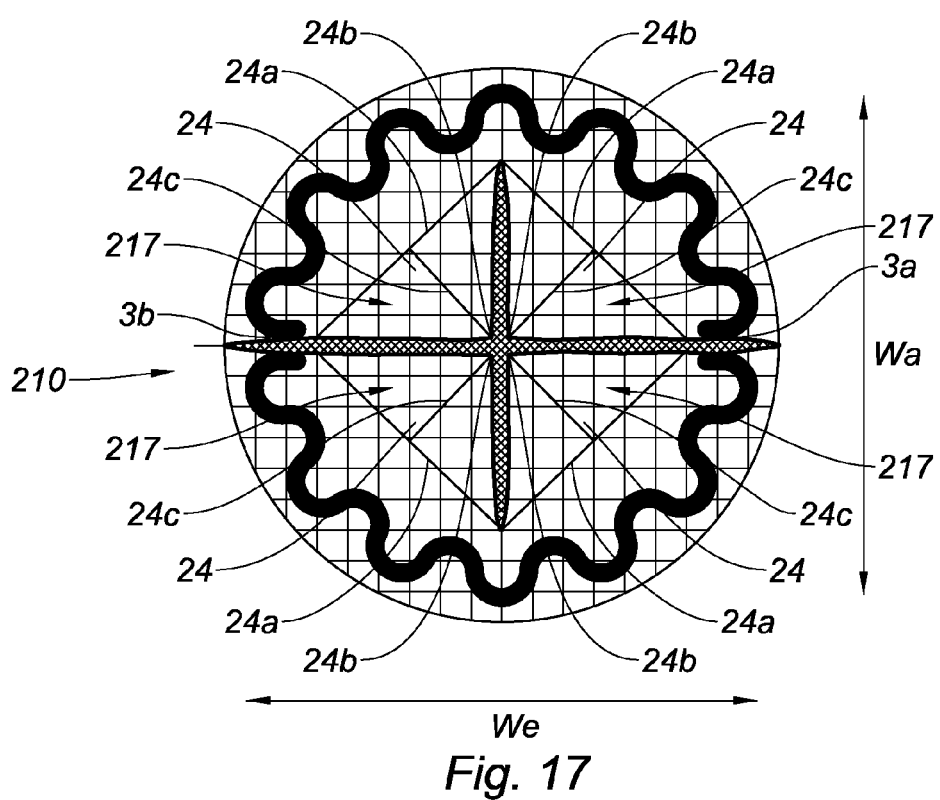

With reference to FIG. 14, is shown a textile 20 for forming the widened parts 217 of tongues of the prosthesis 210 (see FIG. 17). On the example shown, the textile 20 has the shape of a square, the length of one side of the square being greater than the greater diameter of the intended resulting prosthesis 210. This textile 20 may be identical to that forming the mesh 1 or different. The textile 20 is for example produced on a knitting machine and has a warp direction Wa and a weft direction We, as shown on this FIG. 14. The textile 20 may have different mechanical properties, such as elongation and tensile strength, along its warp direction Wa and along its weft direction We.

Preferably, the textile 20 has a colour different from that of the mesh 1.

Figure 15:
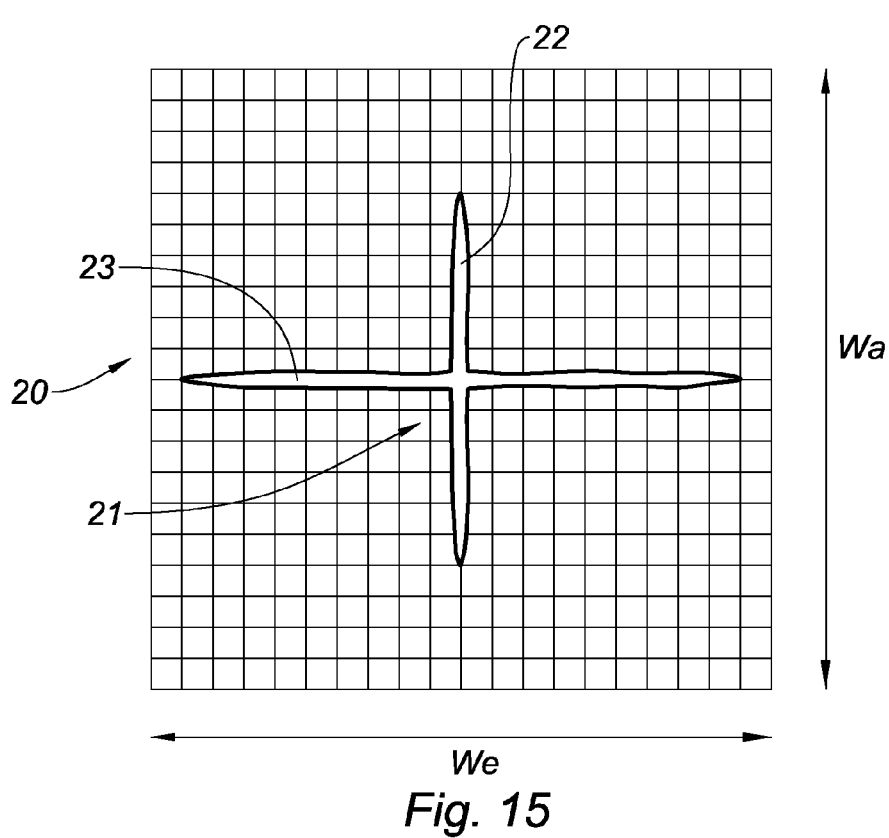

In order to proceed with the manufacturing of the four widened parts 217, a cutting 21 having the shape of a cross with two perpendicular branches (22, 23) is completed on textile 20, with one branch 22 of the cross parallel to the warp direction Wa and the other branch 23 of the cross parallel to the weft direction We, as shown on FIG. 15. The branches of the cross may be of identical lengths or not. On the example shown on FIG. 15, the length of the branch 22 parallel to the warp direction Wa is smaller than the length of the branch 23 parallel to the weft direction. In addition, on this example and as will appear from FIG. 16, the length of the branch 22 parallel to the warp direction Wa is smaller than the diameter of the internal perimeter of the frame 2, whereas the length of the branch 23 parallel to the weft direction is greater than the diameter of the outer perimeter of the frame 2.

In a further step, the textile 20 is laid upon a piece of mesh 1, for example of similar square shape and dimensions as the textile 20, and the frame 2 of FIG. 4 is then welded to both the mesh 1 and the textile 20.

Figure 16:
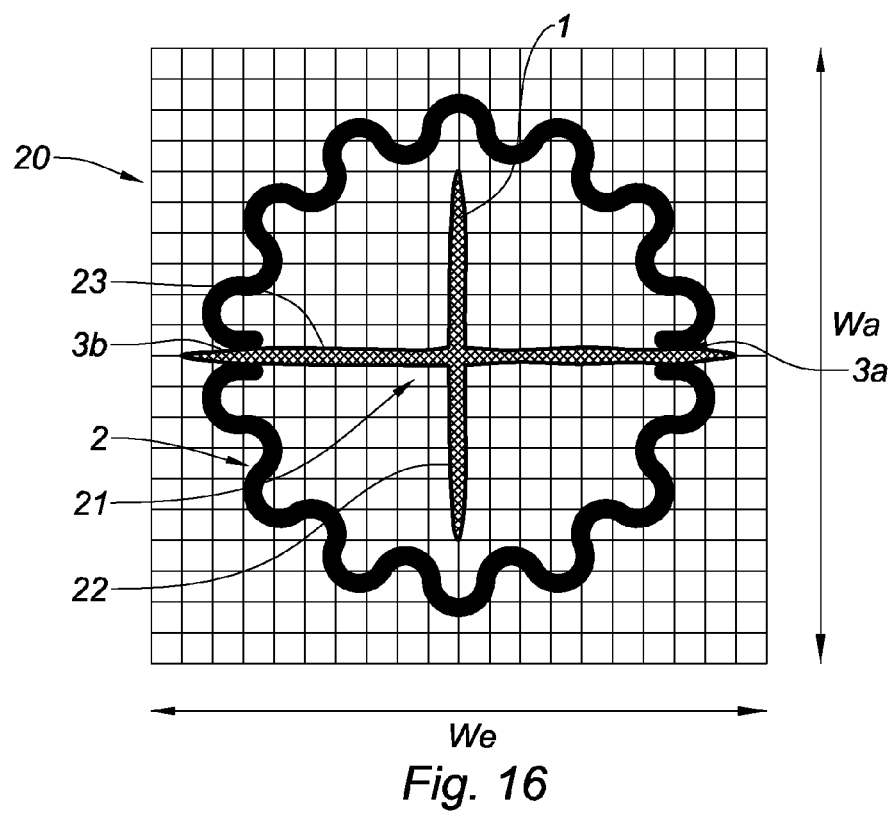

As shown on FIG. 16, the frame 2 is welded on mesh 1 and textile 20 so that the greater branch 23 of the cutting 21 is applied on the folding line M defined by the frame 2 (see FIG. 4) and extends beyond the hinge points (3a, 3b) of the frame 2, whereas the smaller branch 22 of the cutting 21 does not reach the frame 2. Such an embodiment allows a better efficiency of the frame 2, which may not be damaged by residual filaments coming from the cutting of branch 22 when said frame 2 is welded on both the mesh 1 and the textile 20.

Once the frame 2 is welded, the disc-shape prosthesis 210 may be manufactured by cutting the mesh 1 and textile 20 in excess beyond the outer peripheral border of the frame 2, as shown on FIG. 17. As appears from this Figure, the frame 2 forms together with the cross-shaped cutting 21 four isosceles triangles 24, more or less fixed to the frame 2 by their respective base 24a and free at their vertex angle 24b. These four isosceles triangles 24 of textile 20 form the widened parts 217 of the tongues (not shown) of the prosthesis 210.

As mentioned above, a rectangular part such as rectangular part 6 of tongue 5 of FIG. 5 may then be attached to the free vertex angle 24b of each triangle 24 by any fixation means such as sewing, welding, gluing or by means of a gripping textile, in line with the direction defined by the altitude 24c drawn from the vertex angle 24b of each triangle 24.

Because of the specific cross-shaped cutting 21, with one branch parallel to the warp direction Wa and the other branch parallel to the weft direction We, all four isosceles triangles 24 of textile 20 are identical and they all show the same mechanical properties, such as elongation properties and tensile strength properties, each in the direction of its altitude 24c corresponding to the centripetal direction of the disc-shape prosthesis 210, regardless from the fact that the initial elongation and tensile strength properties of the textile 20 in its warp direction Wa were identical or not to its initial elongation and tensile strength properties in the weft direction We.

Indeed, because of the location of the cutting 21 with respect to the frame 2 during the welding step, the altitude direction or centripetal direction for each triangle 24 forms an angle of 45° with respect to both warp and weft directions of the initial textile 20.

As a consequence, all four widened parts 217 show the same mechanical properties, in particular elongation properties and tensile strength properties, in the direction corresponding to the direction of the altitude 24c of each triangle 24, in other words in the direction of the rectangular part of the tongue (not shown) corresponding to the direction of the traction exerted by the surgeon when he puts the prosthesis in place and fixes it to the abdominal wall.

As a consequence, when the surgeon pulls on the rectangular parts of the four tongues at the time he puts the prosthesis 210 in place and fixes it to the abdominal wall, all widened parts 217 of the tongues react similarly and the traction exerted by the surgeon on the whole prosthesis 210 via the four tongues is equally distributed. The prosthesis 210 is therefore properly positioned. In addition, because the four isosceles triangles 24 of textile 20 have a colour different from that of the mesh 1, the surgeon readily identifies the stitching line as defined above. The step of fixing the prosthesis 210 to the abdominal wall is therefore facilitated.

The method of manufacturing the prosthesis 210 described above is very simple and allows starting from a single piece of textile 20 for manufacturing the four widened parts 217.

Alternatively, the prosthesis 210 may be manufactured by preparing initially four separate triangles 24 of textile 20 and welding each triangle 24 to the mesh 1 via the frame 2, or alternatively by preparing two pieces of semi-discs of textile 20, completing a perpendicular cutting on each semi-disc and welding the two cut semi-discs to the mesh via the frame 2.

Like the prosthesis 200 of FIGS. 1-13, the prosthesis 210 of FIG. 17 may be provided with a centring thread 13 and may be coated on the face of the mesh 1 opposite that including the widened parts 217 with a non-adherent coating 201.

The fitting of a prosthesis of the invention, for example the prosthesis 200 from FIG. 8B, is described next with reference to FIGS. 9 to 11. Although not described, the fitting of the prosthesis 210 of FIG. 17 may be completed in the same manner as that described hereinafter for prosthesis 200 of FIG. 8B.

After making the incision 110 described with reference to FIG. 2, the surgeon grasps the prosthesis 200 from FIG. 8B, covered with a non-adherent coating 201 on the face of the mesh 1 opposite that including the tongues 5, and applies force to the prosthesis 200 with his fingers to fold it along the folding line M. Because of the presence of the two hinge points 3a and 3b, this operation is without difficulty and totally independent of the elastic or non-elastic nature of the frame 2. In the embodiment shown, the prosthesis 200 being a disc, it is folded along one of its diameters, resulting in two identical parts. In this folded configuration, the prosthesis 200 occupies a small volume and the surgeon may easily introduce it into the abdominal cavity 109, as shown in FIG. 9, while holding the centring thread 13 outside the body of the patient. For clarity, the fingers of the surgeon are not represented in FIGS. 9 to 11.

Once the prosthesis 200 is in the abdominal cavity 109, the surgeon releases the pressure on it. It is the surgeon who manually deploys the prosthesis 200 in a perfectly tensioned and spread out configuration. Thus, the prosthesis 200 being able to adopt only two positions, namely folded in two or spread out, the surgeon is certain that the prosthesis is perfectly spread out from the moment of unfolding the prosthesis 200.

In the next step, as shown in FIG. 10A, the surgeon uses the centring thread 13 both to centre the prosthesis 200 relative to the incision 110 and to press the prosthesis 200 against the abdominal wall (101, 104). To this end, the surgeon pulls the centring thread 13 toward the exterior of the body of the patient. Thus the prosthesis 200 is spread perfectly and there is no risk of the viscera being disposed between the widened parts 7 of the tongues 5 and the abdominal wall (101, 104).

Once the prosthesis 200 is correctly positioned relative to the hernia defect, the surgeon withdraws the centring thread 13, thereby releasing the free ends 6b of the tongues 5, as shown in FIG. 10B.

In doing this, the surgeon raises a part of the edge of the hernia and thus uncovers a central area 12 in the vicinity of the prosthesis 200, delimited overall by the widened parts 7 of the tongues 5, which area the surgeon may easily view and in which the surgeon is able to work easily. In one embodiment, the widened parts 7 of the tongues 5 or the tongues 5 as a whole may be a different colour than the mesh 1, in order to facilitate viewing of the central working area 12 by the surgeon. Indeed, the colour difference between the widened parts 7 of the tongues, or the whole tongues 5, and the mesh 1 defines a line, said line pointing out to the surgeon where to complete the stitches for fixing the prosthesis 200 to the abdominal wall. This fixing line, or stitching line, globally corresponds to the interior contour of the frame 2.

In a following step, as shown in FIG. 10B, the surgeon proceeds to fix the prosthesis 200 to the biological tissues by using a needle 9 and a suture 10 to suture the enlarged part 7 of each tongue 5 to the abdominal wall 101, 104 within the central working area 12. During this step, the whole of the prosthesis 200 remains perfectly spread out and perfectly pressed onto the abdominal wall 104, notably by virtue of the presence of the undulations 4 of the frame 2, which smooth out deformations caused by the surgeon in the area of the prosthesis 200 that is in the process of being sutured. The surgeon may execute one or more stitches 11 (see FIG. 11) for each enlarged part 7 of the four tongues 5.

As may be seen in FIG. 11, the structure of the prosthesis 200 of the invention enables the surgeon to place the stitches 11 in an area situated between the centre of the mesh 1 and the exterior peripheral edge 1a thereof; this area is in particular located at the level of the interior contour of the frame 2: thus the surgeon does not have to execute stitches at the exterior peripheral edge of the mesh 1, which can be viewed only with difficulty because of the small size of the incision 110. The mesh 1 nevertheless remains perfectly pressed against the abdominal wall 104 along this peripheral edge 1a because of the presence of the frame 2. Nevertheless, because of the structure of the prosthesis 200 of the invention, the stitches 11 are advantageously situated at some distance from the defect, in particular in an area more or less in the middle between the centre 1b of the mesh (which is the location of the hernia defect) and the peripheral exterior edge 1a of the mesh, at a location where the biological tissues are often healthier and less fragile than at the margin of the defect. The stitches 11 may for example be U-shaped, i.e. obtained with a thread provided with a needle at each of its ends.

Once the surgeon has executed the necessary stitches 11 over all the widened parts 7, each tongue 5 is cut approximately at the junction 6a between its widened part 7 and its rectangular part 6 in order to retain at the implantation site only the widened portion 7, as shown in FIG. 11. This figure shows the stitches 11 that fix the widened parts 7 of the tongues 5 to the abdominal wall 104. As may be seen in FIG. 11, the prosthesis 200 is thus perfectly deployed, spread out and pressed against the abdominal wall (101, 104) with no risk of trapping viscera between the prosthesis 200 and the abdominal wall (101, 104).

The surgeon then has only to close the incision 110 in the conventional way for small size hernias, i.e. by stitches. During this operation, the rectangular parts 6 of the tongues 5 cannot impede the surgeon because they have advantageously been cut off and removed beforehand.

FIG. 12 shows a variant of an embodiment of the tongues of the prosthesis of the invention. As shown in FIG. 12, two opposed tongues 5 may be produced from a single rectangular piece of textile 14 provided at its two ends with two widened parts 7. The part 14 is fixed to the mesh 1 by the widened parts 7 as explained above for the embodiment of FIGS. 1 to 11. If a final prosthesis provided with four tongues is required, a second piece 14 of textile is fixed to the mesh 1, perpendicularly to the first piece. A centring thread may be passed through the centres of the two textile parts 14. Once the prosthesis has been positioned correctly at the implantation site, as shown in FIG. 13, in which only one textile part 14 is shown, the surgeon has only to cut each textile part 14 at its centre in order to obtain two opposed tongues: the surgeon can then continue fixing the prosthesis as shown in FIGS. 10B and 11.

The prosthesis of the invention is particularly simple to install, the surgeon being easily able to uncover a comfortable working area, despite the restricted size of the implantation site. The fitting of the prosthesis of the invention is also particularly reliable, all risk of trapping the viscera being avoided. A prosthesis of the invention is particularly suitable for treating umbilical hernias where the abdominal incision made is of small size. The prosthesis of the invention is adapted to adopt a configuration in which it occupies a particularly small volume facilitating its introduction into the abdominal cavity via a small incision without necessitating the use of any dedicated ancillary device. Thanks to its particular structure, the prosthesis of the invention may be spread out and pressed onto the abdominal wall efficaciously, also without necessitating the use of a dedicated tool to assist spreading it and with no risk of reversion of the prosthesis. The prosthesis of the invention thus makes it possible to treat a hernia, in particular an umbilical hernia, efficaciously, simply and rapidly, minimizing the risk of relapse.

The invention claimed is:
1. A prosthesis comprising:
at least one flexible mesh delimited by a peripheral exterior edge,
at least two tongues extending from one face of the mesh, and
at least one reinforcing member which takes the form of a frame fastened to said mesh and substantially adopting the shape of said peripheral exterior edge of the mesh, said frame being set back from said peripheral exterior edge and being provided with two hinge points made of a biocompatible material, a folding line passing through said two hinge points also passing through the center of the mesh for folding the mesh in two.
2. The prosthesis according to claim 1, wherein the frame set back from the peripheral external edge is of serpentine shape forming undulations.

3. The prosthesis according to claim 2, wherein said frame takes the form of a flat ribbon forming undulations substantially in a plane of said mesh.

4. The prosthesis according to claim 1, wherein said reinforcing member is produced in bioresorbable material.

5. The prosthesis according to claim 1, wherein said tongues have a rectangular shape part and a widened part provided at one end of the rectangular part, said widened part of said tongues fixed to said mesh.

6. The prosthesis according to claim 5, wherein the widened part being separate from the rest of the tongue, said widened part is produced in gripping textile so that said widened part may be fastened to and/or unfastened from the rest of the tongue at will.

7. The prosthesis according to claim 5, wherein the widened parts of the tongues are of a color different from that of the mesh.

8. The prosthesis according to claim 5, wherein said widened part of each tongue is under the form of isosceles triangles of textile, each triangle being fixed to said mesh via its base, all four triangles showing identical elongation and tensile strength properties in the centripetal direction.

9. The prosthesis according to claim 1, wherein said tongues are a textile.

10. The prosthesis according to claim 1, wherein said two tongues are fixed symmetrically to either side of said folding line.

11. The prosthesis according to claim 1, wherein said mesh is disc-shaped, said frame being substantially in the form of a circular ring, said tongues are fixed at two diametrically opposite places of said ring, said two places being spaced by 90° from each of said two hinge points.

12. The prosthesis according to claim 11, wherein the face of the mesh including said two tongues has two additional tongues fixed to the mesh at the location of two hinge points of the ring.

13. The prosthesis according to claim 1, wherein the face of the mesh opposite that including said tongues is covered by a non-adherent coating.

14. The prosthesis according to claim 1, wherein a free end of each tongue is joined together by means of a centering thread.

15. The prosthesis according to claim 1, wherein at least a portion of the tongues is of a color different from that of the mesh.

16. The prosthesis according to claim 1, wherein said mesh being disc-shaped and said frame being substantially in the form of a circular ring, said prosthesis comprises four of said tongues, a widened part of each tongue being of a color different from that of the mesh, and being distributed along an interior contour of said ring, symmetrically with respect to said folding line two of said widened parts on one side of said folding line, the other two of said widened parts on the other side of said folding line.

17. The prosthesis according to claim 1, wherein the hinge points lack elasticity.

18. The prosthesis according to claim 1, the frame comprises two semicircles connected to each other by the hinge points.

19. The prosthesis according to claim 18, wherein the two semicircles include undulations.

20. The prosthesis according to claim 18, wherein the hinge points bridge the two semicircles.

* * * * *